US011647747B2

(12) United States Patent
Li et al.

(10) Patent No.: US 11,647,747 B2
(45) Date of Patent: *May 16, 2023

(54) PEROXYFORMIC ACID COMPOSITIONS FOR MEMBRANE FILTRATION CLEANING IN ENERGY SERVICES

(71) Applicant: ECOLAB USA INC., Saint Paul, MN (US)

(72) Inventors: Junzhong Li, Saint Paul, MN (US); Cynthia Bunders, Saint Paul, MN (US); Richard Staub, Saint Paul, MN (US); Paul Frazer Schacht, Saint Paul, MN (US); Caleb Power, Saint Paul, MN (US); Ramakrishnan Balasubramanian, Saint Paul, MN (US); Robert J. Ryther, Saint Paul, MN (US); Catherine Hanson, Saint Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 36 days.

This patent is subject to a terminal disclaimer.

(21) Appl. No.: 17/302,678

(22) Filed: May 10, 2021

(65) Prior Publication Data

US 2021/0282397 A1 Sep. 16, 2021

Related U.S. Application Data

(63) Continuation of application No. 16/559,894, filed on Sep. 4, 2019, now Pat. No. 11,026,420, which is a continuation of application No. 15/623,024, filed on Jun. 14, 2017, now Pat. No. 10,524,470.

(60) Provisional application No. 62/434,981, filed on Dec. 15, 2016.

(51) Int. Cl.
*A61L 2/18* (2006.01)
*A01N 37/16* (2006.01)

(52) U.S. Cl.
CPC .............. *A01N 37/16* (2013.01); *A61L 2/18* (2013.01); *A61L 2/186* (2013.01); *A61L 2202/17* (2013.01)

(58) Field of Classification Search
CPC .................................. A61L 2/18; A61L 2/186
See application file for complete search history.

(56) References Cited

U.S. PATENT DOCUMENTS

| | | |
|---|---|---|
| 5,616,335 A | 4/1997 | Nicolle et al. |
| 6,139,756 A | 10/2000 | Fuchs et al. |
| 6,211,237 B1 | 4/2001 | Huss et al. |
| 6,254,801 B1 | 7/2001 | Reinold et al. |
| 6,284,719 B1 | 9/2001 | Simms |
| 6,468,472 B1 | 10/2002 | Yu et al. |
| 7,638,067 B2 | 12/2009 | Hilgren et al. |
| 7,915,445 B2 | 3/2011 | Maatta et al. |
| 8,802,061 B2 | 8/2014 | Tichy et al. |
| 8,828,910 B2 | 9/2014 | Aksela et al. |
| 8,877,354 B2 | 11/2014 | Horiuchi et al. |
| 9,044,403 B2 | 6/2015 | Shultz |
| 9,192,909 B2 | 11/2015 | Kraus et al. |
| 9,617,170 B2 | 4/2017 | Karpova et al. |
| 10,457,850 B2 | 10/2019 | Sun et al. |
| 2002/0177732 A1 | 11/2002 | Pohjanvesi et al. |
| 2004/0143133 A1 | 7/2004 | Smith et al. |
| 2006/0177518 A1 | 8/2006 | Stevenson et al. |
| 2007/0023363 A1 | 2/2007 | Daines et al. |
| 2007/0056904 A1 | 3/2007 | Hogt et al. |
| 2007/0249712 A1 | 10/2007 | Dee et al. |
| 2009/0200234 A1 | 8/2009 | Schacht et al. |
| 2009/0221704 A1 | 9/2009 | Aksela et al. |
| 2009/0320214 A1 | 12/2009 | Shamayeli et al. |
| 2010/0084340 A1 | 4/2010 | Monsrud et al. |
| 2011/0094044 A1 | 4/2011 | Shamayeli et al. |
| 2012/0228221 A1 | 9/2012 | Kakigami et al. |
| 2013/0079733 A1 | 3/2013 | Burt et al. |
| 2013/0203849 A1 | 8/2013 | Ben Yehuda |
| 2014/0039050 A1 | 2/2014 | da Costa et al. |
| 2014/0097144 A1 | 4/2014 | Li et al. |
| 2014/0124461 A1 | 5/2014 | Buisson et al. |
| 2014/0274857 A1 | 9/2014 | Schacht et al. |
| 2014/0367334 A1 | 12/2014 | Salonen et al. |
| 2015/0018319 A1 | 1/2015 | Larson et al. |
| 2015/0056679 A1 | 2/2015 | Patten et al. |
| 2015/0183673 A1 | 7/2015 | Musale et al. |
| 2015/0240328 A1 | 8/2015 | Urbani |

(Continued)

FOREIGN PATENT DOCUMENTS

| | | | |
|---|---|---|---|
| AU | 2007311532 A1 | 4/2008 | |
| CA | 2131664 A1 | 3/1995 | |

(Continued)

OTHER PUBLICATIONS

Johnson, Greg, et al. "Kinetics of Mineral Scale Membrane Fouling" Technical Article, 14 pages, accessed from www.vsep.com as of Dec. 1, 2016.

Vance, Frederick W., et al. "New Solution for Controlling of Organic and BioFouling in High Pressure Membrane Applications" AMTA/AWWA Membrane Technology Conference & Exposition 2013, San Antonio, Texas, Feb. 25-28, vol. 2 of 2, 14 pages Feb. 25, 2013.

(Continued)

*Primary Examiner* — Bradley R Spies
(74) *Attorney, Agent, or Firm* — McKee, Voorhees & Sease, PLC

(57) ABSTRACT

Peroxyformic acid compositions for treatment and removal of biofilm growth and mineral deposits on membranes for energy services applications are disclosed. In particular, peroxyformic acid compositions are generated in situ or on site generation for the reduction and prevention, of biofilms and the mitigation of mineral buildup on the membranes. The compositions according to the invention are compatible with the membranes under application of use conditions.

18 Claims, 8 Drawing Sheets

(56) References Cited

U.S. PATENT DOCUMENTS

| | | |
|---|---|---|
| 2015/0351383 A1 | 12/2015 | Kolari et al. |
| 2015/0351389 A1 | 12/2015 | Kolari et al. |
| 2016/0068417 A1 | 3/2016 | Buschmann |
| 2016/0176814 A1 | 6/2016 | Balasubramanian et al. |

FOREIGN PATENT DOCUMENTS

| | | |
|---|---|---|
| CA | 2300807 A1 | 9/2000 |
| CA | 2475361 A1 | 8/2003 |
| CA | 3009259 A1 | 6/2017 |
| CN | 101054779 B | 5/2012 |
| CN | 102876287 B | 6/2014 |
| CN | 104206413 A | 12/2014 |
| CN | 107925112 A | 4/2018 |
| DE | 3504394 A1 | 9/1985 |
| EP | 0231632 A2 | 8/1987 |
| EP | 0231632 A3 | 8/1987 |
| EP | 1022946 B1 | 8/2000 |
| EP | 1247802 A1 | 10/2002 |
| EP | 1125497 A2 | 6/2003 |
| EP | 1244842 B1 | 1/2004 |
| EP | 1131016 B1 | 2/2005 |
| EP | 2609990 A1 | 7/2013 |
| EP | 2653448 B1 | 2/2018 |
| EP | 3169844 B1 | 12/2018 |
| FI | 113056 B | 2/1999 |
| FI | 126082 B | 7/2014 |
| JP | 60175504 A | 9/1985 |
| JP | 2000117069 A | 4/2000 |
| JP | 2005154551 A | 6/2005 |
| JP | 2008100161 A | 5/2008 |
| WO | 9420424 A1 | 9/1994 |
| WO | 9517241 A1 | 6/1995 |
| WO | 9623858 A1 | 8/1996 |
| WO | 9719594 A1 | 6/1997 |
| WO | 9856988 A1 | 12/1998 |
| WO | 9946234 A1 | 9/1999 |
| WO | 2000045639 A1 | 8/2000 |
| WO | 0170030 A2 | 9/2001 |
| WO | 0170030 A3 | 9/2001 |
| WO | 03092919 A1 | 11/2003 |
| WO | 2005005028 A1 | 1/2005 |
| WO | 2007031596 A2 | 3/2007 |
| WO | 2007031596 A3 | 3/2007 |
| WO | 2007070609 A2 | 6/2007 |
| WO | 2008056025 A3 | 5/2008 |
| WO | 2008088873 A1 | 7/2008 |
| WO | 2008120509 A1 | 10/2008 |
| WO | 2011006019 A2 | 1/2011 |
| WO | 2012025943 A1 | 3/2012 |
| WO | 2012025943 A4 | 3/2012 |
| WO | 2012113042 A1 | 8/2012 |
| WO | 2012177366 A2 | 12/2012 |
| WO | 2012177366 A3 | 12/2012 |
| WO | 2013051013 A2 | 4/2013 |
| WO | 2013098478 A2 | 7/2013 |
| WO | 2013098479 A1 | 7/2013 |
| WO | 20130175062 A1 | 11/2013 |
| WO | 2013184605 A1 | 12/2013 |
| WO | 2014062487 A1 | 4/2014 |
| WO | 2014154946 A1 | 10/2014 |
| WO | 2016100694 A1 | 6/2016 |
| WO | 2016100700 A1 | 6/2016 |
| WO | 2017106623 A1 | 6/2017 |
| WO | 2017181005 A1 | 10/2017 |
| WO | 2017194842 A1 | 11/2017 |
| WO | 2018091784 A1 | 5/2018 |

OTHER PUBLICATIONS

DeJong, Robert L., "Atmospheric Corrosion Problems in Secondary Fibre Plants", Enzyme Microb. Technol. (Jul. 1979) vol. 1, p. 205-209.

Littlejohn, et al., "Removal of NOx and SO2 from Flue Gas by Peracid Solutions", Ind. Eng. Chem. Res. (1990) 29, pp. 1420-1424.

Ecolab USA Inc., PCT/US2017/037467 filed Jun. 14, 2017, "Notification of Transmittal of the International Search Report and the Written Opinion of the International Searching Authority, or the Declaration", dated Sep. 5, 2017.

Ecolab USA, Inc., PCT/US2017/027622 filed Apr. 15, 2016, "International Search Report", dated Jul. 27, 2016.

Ecolab USA Inc., PCT/US2016/067139 filed Dec. 16, 2016, "The International Search Report and The Written Opinion of the International Searching Authority, or the Declaration", dated Jun. 1, 2017.

European Patent Office, "Extended European Search Report", in connection with PCT/US2016/067139 filed Dec. 16, 2016, 8 pages, dated Jun. 28, 2019.

PEROXYFORMIC ACID COMPOSITIONS FOR MEMBRANE FILTRATION CLEANING IN ENERGY SERVICES

CROSS REFERENCE TO RELATED APPLICATIONS

This is a Continuation Application of U.S. Ser. No. 16/559,894, filed Sep. 4, 2019, which is a Continuation Application of Non-Provisional U.S. application Ser. No. 15/623,024, filed Jun. 14, 2017, now U.S. Pat. No. 10,524,470 issued Jan. 7, 2020, which claims priority under 35 U.S.C. § 119 to U.S. Ser. No. 62/434,981 filed Dec. 15, 2016, all of which are herein incorporated by reference in their entirety.

FIELD OF THE INVENTION

The invention relates to use of peroxyformic acid compositions for removal of biofilm growth and mineral deposits on membranes. Accordingly, the present invention relates to the field of membrane separation processes and clean in place or wash composition for cleaning such membranes, including removal of minerals and biofilms through the use of an antimicrobial wash. In particular, peroxyformic acid compositions are generated in situ or by on site generation for the reduction, removal and/or kill of biofilms and the mitigation of mineral buildup on the membranes. The compositions according to the invention are unexpectedly compatible with the membranes under application of use conditions.

BACKGROUND OF THE INVENTION

Various technologies use membranes, including those membranes that apply reverse osmosis. A disadvantage in the use of membranes is that during operation, the membranes gradually become fouled. In particular, biofilm growth and mineral deposits on membranes, including reverse osmosis membranes, nanofiltration membranes, ultrafiltration membranes, and microfiltration membranes, can have detrimental results. Such biofilm growth and mineral deposits can cause severe flux declines, increased pressure, reduced production, can negatively impact the quality of finished goods, and often results in premature replacement of such membranes.

Membranes provided within a separation facility can be treated using clean-in-place (CIP) methods to provide flushing, rinsing, pretreatment, cleaning, and preserving, as filtration membranes have a tendency to foul during processing. Fouling manifests itself as a decline in flux and an increase in pressures with time of operation leading to decreased production. Flux decline is typically a reduction in permeation flow or permeation rates that occurs when all operating parameters, such as pressure, feed flow rate, temperature, and feed concentration are kept constant. In general, membrane fouling is a complicated process and is believed to occur due to a number of factors including electrostatic attraction, hydrophobic and hydrophilic interactions, the deposition and accumulation of feed components, e.g., suspended particulates, impermeable dissolved solutes, and even normally permeable solutes, on the membrane surface and/or within the pores of the membrane. It is expected that almost all feed components will foul membranes to a certain extent. See Munir Cheryan, Ultrafiltration and Microfiltration Handbook, Technical Publication, Lancaster, Pa., 1998 (Pages 237-288). Fouling components and deposits can include inorganic salts, particulates, microbials and organics.

Filtration membranes typically require periodic cleaning to allow for successful industrial application within separation facilities such as those found in the food, dairy, beverage and energy industries. The filtration membranes can be cleaned by removing foreign material from the surface and body of the membrane and associated equipment. The cleaning procedure for filtration membranes can involve a clean-in-place CIP process or in situ cleaning where cleaning agents are circulated over and through the membrane to wet, soak, penetrate, dissolve and/or rinse away foreign materials from the membrane. Various parameters that can be manipulated for cleaning typically include time, temperature, mechanical energy, chemical composition, chemical concentration, soil type, water type, hydraulic design, and membrane materials of construction.

Conventional cleaning techniques include the use of high heat and/or extreme pH, i.e., very high alkalinity use solutions, or very low pH acidic use solutions. However, many surfaces cannot tolerate such conditions. For example, membranes used in the energy services industry often have specific limitations with respect to the temperature and pH at which they can be operated and cleaned due to the material from which they are constructed.

In general, the frequency of cleaning and type of chemical treatment performed on the membrane has been found to affect the operating life of a membrane. It is believed that the operating life of a membrane can be decreased as a result of chemical degradation of the membrane over time. Various membranes are provided having temperature, pH, and chemical restrictions to minimize degradation of the membrane material. For example, many polyamide reverse osmosis membranes have chlorine restrictions because chlorine can have a tendency to halogenate and damage the membrane. Cleaning and sanitizing filtration membranes is desirable in order to comply with laws and regulations that may require cleaning in certain applications (e.g., oil and gas production), reduce microorganisms to prevent contamination of the product streams, and optimize the process by restoring flux (and pressure).

Both oxidizing and non-oxidizing biocides are conventionally used in combination with alkaline treatments for disinfection of a membrane and to prevent or reduce the fouling of the membrane. Exemplary oxidizing agents are chloric compounds, which are known to have strong antimicrobial effects, however they have a significant disadvantage in that they may damage the membrane surface. Such contact with membrane surfaces is a required part of the disinfectant process using the oxidizing biocide. Other exemplary techniques for cleaning membranes are disclosed by U.S. Pat. No. 4,740,308 to Fremont et al.; U.S. Pat. No. 6,387,189 to Groschl et al.; and U.S. Pat. No. 6,071,356 to Olsen; and U.S. Publication No. 2009/0200234.

Various methods of cleaning membranes are known to decrease the lifespan of a membrane as a result of damaging the membranes and surrounding equipment that is to be cleaned. For example, an acid treatment might have a corrosive effect on the surfaces of process equipment and on filtration membranes used therein. Also, the rather high temperature required entails an increase in energy costs. Furthermore, the use of large volumes of acidic inactivation compositions requires their neutralization and proper disposal of the liquid waste. These and other known disadvantages of membrane cleaning systems are known.

In the context of energy services, there are additional concerns regarding water sources and the compatibility of these with the peroxyformic acid compositions of the invention for cleaning membranes. In an aspect, in the context of offshore oil and gas facilities there are concerns regarding the water sources available, namely sea water, brine water, brackish water and produced water. The additional presence of ions such as chloride, divalent metals and sulfate can further damage the membrane and present issues in terms of compatibility of treatment and cleaning protocols with the membrane material. Further, the complex diversity of the species of microbes present in these waters can lead to an increase in biological fouling and the accumulation of biofilm on membrane surfaces. These are exemplary concerns uniquely present in the treatment of membranes for energy services applications. These concerns illustrate the need for membranes to separate out many species in sea water and other conditions used in oil and gas platforms. In particular, it is a need to use membranes to separate out sulfate from seawater in an oil and gas open sea platform.

Although various agents preventing microbial growth, such as oxidizers, have been used for membrane cleaning there is still a need for an improved method for the prevention of microbial growth and biofilm formation on membranes.

Accordingly, it is an objective of the claimed invention to provide peroxyformic acid compositions generated in situ for the prevention of mineral scale formation, deposit build up and removal of microbial growth on membranes and biofouling of membranes. In particular, it is an object of the invention to provide a method, which does not damage the membranes and which mitigates microbial growth and biofouling on the membranes.

A further object of the invention is to replace 2,2-dibromo-3-nitrilopropionamide (DBNPA), a traditional biocide that hydrolyzes under both acidic and alkaline conditions, with the peroxyformic acid compositions according to the invention.

A further object of the invention is to provide a membrane-compatible composition, such that the composition does not contain any components destroying or blocking the membrane, and/or generate chlorine species causing damage to membranes.

Other objects, advantages and features of the present invention will become apparent from the following specification taken in conjunction with the accompanying drawings.

BRIEF SUMMARY OF THE INVENTION

An advantage of the invention is a membrane compatible peroxycarboxylic acid composition comprising peroxyformic acid composition generated in situ or on site for use to remove and/or reduce biofilm growth and mineral deposits on membranes. It is an advantage of the present invention that the cleaning compositions are biodegradable, decompose into non-hazardous products, which therefore leave no toxic traces on the treated membranes (due to rapid degradation into water, carbon dioxide and formic acid which are recognized as GRAS) and do not negatively interfere with the membranes. Moreover, the peroxyformic acid composition is suitable for generation in situ or on site of a point of use, allowing a user to promptly apply the composition to a membrane in need of treatment to contact the membrane surface and control biofilm growth at the place where the biofilm bacteria adhere and initiate biofilm formation.

In an embodiment, the present invention discloses onsite generated peroxycarboxylic acid compositions comprising compositions of performic acid and/or combinations of performic acid and additional peracids and/or oxidizing chemistries that efficiently kill and removal biofilms and other soils, along with inorganic scale on membranes without damaging or negatively interfering with the membranes treated.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
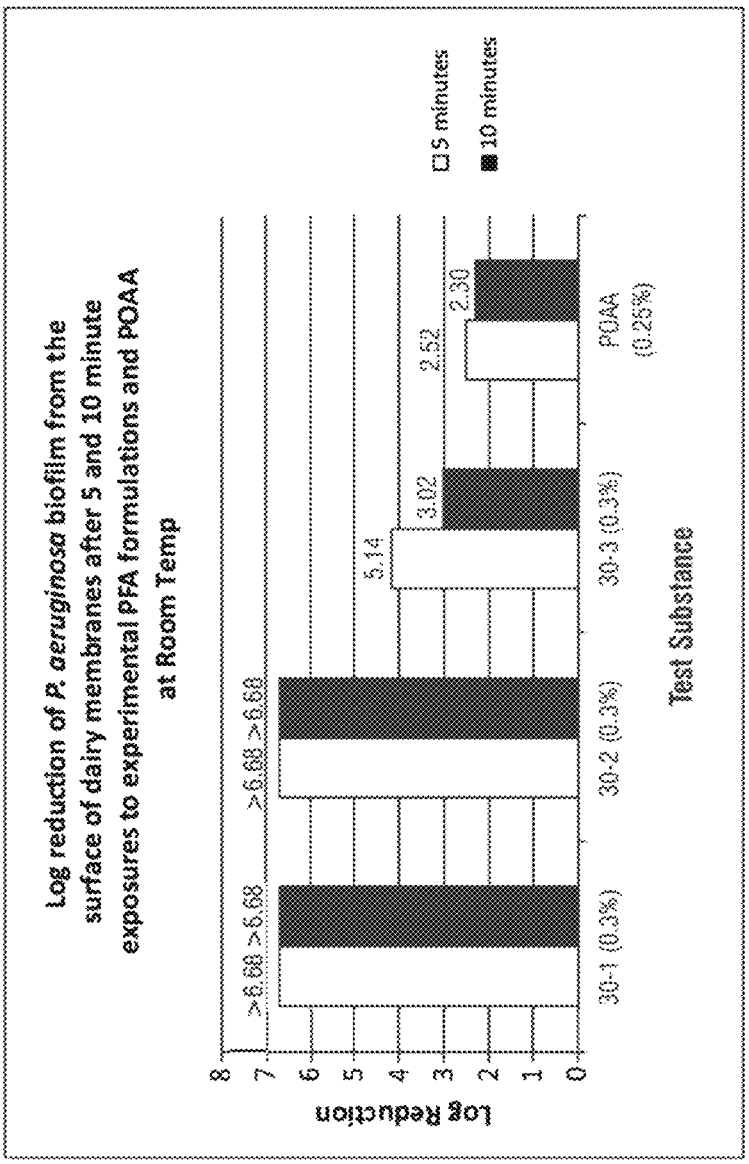
FIG. 1 is a graphical representation showing the average log reduction of *P. aeruginosa* biofilm after exposure to the peroxyformic acid formulations according to an embodiment of the invention.
Figure 2:
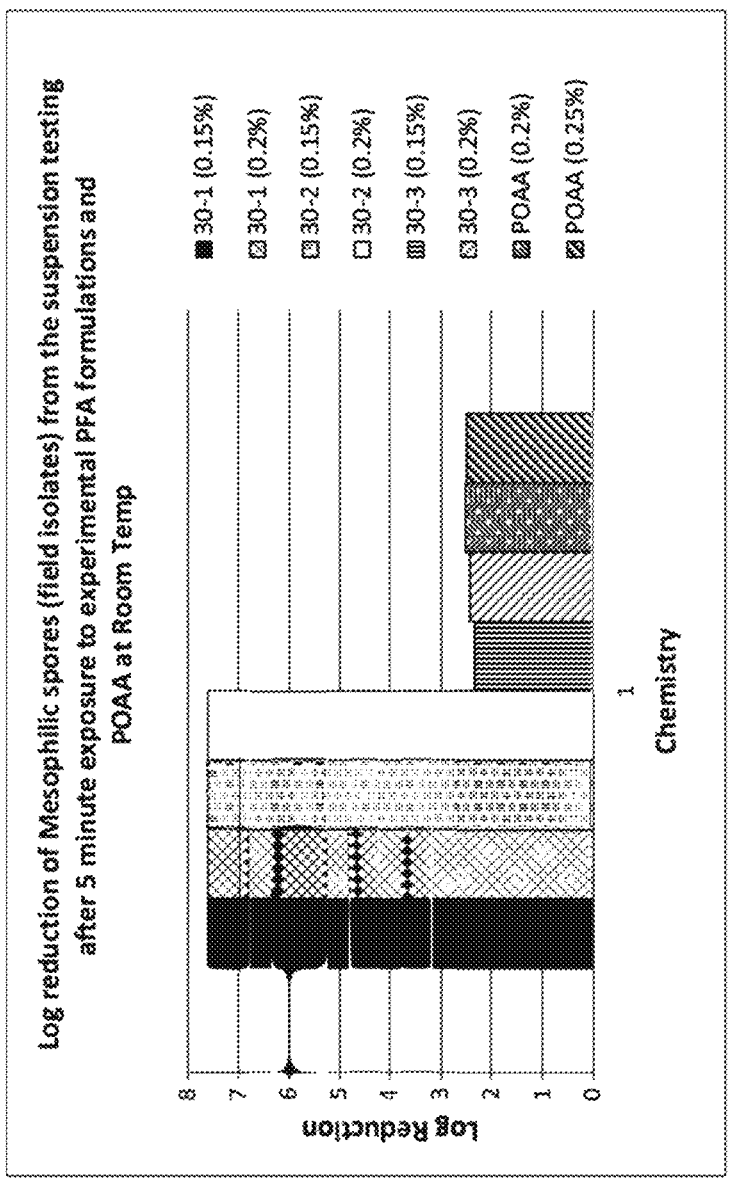
FIG. 2 shows the average log reduction of mesophilic spores after exposure to the peroxyformic acid formulations according to an embodiment of the invention.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The present invention relates to membrane compatible peroxycarboxylic acid composition comprising peroxyformic acid composition generated in situ or on site for use to reduce and/or prevent biofilm growth and mineral deposits on membranes. The embodiments of this invention are not limited to particular peroxyformic acid compositions, which can vary and are understood by skilled artisans based on the disclosure herein of the present invention. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts. The examples embodied in the application may refer to composition or product concentrations as opposed to the actives concentration of the peroxyformic acid as will be readily understood by those skilled in the art by the description thereof.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

As used herein, the term "cleaning" refers to a method used to facilitate or aid in soil removal, bleaching, microbial population reduction, and any combination thereof. As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

The term "hard surface" refers to a solid, substantially non-flexible surface such as a counter top, tile, floor, wall, panel, window, plumbing fixture, kitchen and bathroom furniture, appliance, engine, circuit board, and dish. Hard surfaces may include for example, health care surfaces and food processing surfaces.

The term "incompatibility," as used herein refers to conditions or scenarios in which the chemical nature of the material being filtered is not compatible with the structure of the membrane. Incompatibility of materials can be detrimental to the membrane and lead to reduction in filtration capability, damage to the membrane, complete failure of the membrane, etc. As referred to herein a treatment composition and method that is membrane "compatible" does not cause significant reduction in filtration capability as a result of physical damage to the membrane, which can be measured by a decrease in flux of the membrane beyond the typical flux of a new membrane or a significant decrease in rejection, for example decrease in a monovalent salt in RO permeate, divalent salt in NF permeate, etc. In an aspect, a reduction in filtration capability of more than 1%, 2%, 3%, 4%, 5%, 6%, 7%, 8%, 9%, 10% or more is indicative of incompatibility.

As one skilled in the art shall ascertain, the flux and salt rejection limits for a membrane are specifications supplied by a membrane manufacturer as they can vary with manufacture of the membrane. Accordingly, a treatment composition and method that is membrane "compatible" complies with the supplier specification for the membrane without causing reduction in filtration capability as a result of physical damage to the membrane. In an exemplary embodiment, sulfate rejection membranes (SRU, Sulfate Reduction Unit), the flux can increase with damage or decrease with scale and biofilm contamination but a relative decrease in sulfate salt rejection (i.e. more salt found in the permeate flow), is the primary criteria on efficacy of the system.

The term "membrane" means a structure having lateral dimensions much greater than its thickness though which a mass transfer may occur, membranes may be used to filter liquids.

As used herein, the terms "mixed" or "mixture" when used relating to "percarboxylic acid composition," "percarboxylic acids," "peroxycarboxylic acid composition" or "peroxycarboxylic acids" refer to a composition or mixture including more than one percarboxylic acid or peroxycarboxylic acid For the purpose of this patent application, successful microbial reduction is achieved when the microbial populations are reduced by at least about 50%, or by significantly more than is achieved by a wash with water. Larger reductions in microbial population provide greater levels of protection.

As used herein the term "microbial control" refers to an agent that reduces the number of bacterial contaminants to safe levels as judged by the environmental protection agency. In an embodiment, microbial control agents for use in this invention will provide a microbial reduction equivalent to at least a 1 log and more preferably a reduction equivalent to 3-log order reduction.

As used herein, the term "sanitizer" refers to an agent that reduces the number of bacterial contaminants to safe levels as judged by public health requirements. In an embodiment, sanitizers for use in this invention will provide at least a 3 log reduction and more preferably a 5-log order reduction. These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

As used herein, the term "soil" or "stain" refers to a polar-oily hydrocarbon or a non-polar oily substance which may or may not contain particulate matter such as mineral clays, sand, natural mineral matter, carbon black, graphite, kaolin, environmental dust, etc.

As used in this invention, the term "sporicide" refers to a physical or chemical agent or process having the ability to cause greater than a 90% reduction (1-log order reduction) in the population of spores of *Bacillus cereus* or *Bacillus subtilis* within 10 seconds at 60° C. In certain embodiments, the sporicidal compositions of the invention provide greater than a 99% reduction (2-log order reduction), greater than a 99.99% reduction (4-log order reduction), or greater than a 99.999% reduction (5-log order reduction) in such population within 10 seconds at 60° C.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition The term "substantially similar cleaning performance" refers generally to achievement by a substitute cleaning product or substitute cleaning system of generally the same degree (or at least not a significantly lesser degree) of cleanliness or with generally the same expenditure (or at least not a significantly lesser expenditure) of effort, or both.

As used herein, the term "sulfoperoxycarboxylic acid," "sulfonated peracid," or "sulfonated peroxycarboxylic acid" refers to the peroxycarboxylic acid form of a sulfonated carboxylic acid. In some embodiments, the sulfonated peracids of the present invention are mid-chain sulfonated peracids. As used herein, the term "mid-chain sulfonated peracid" refers to a peracid compound that includes a sulfonate group attached to a carbon that is at least one carbon (e.g., the three position or further) from the carbon of the percarboxylic acid group in the carbon backbone of the percarboxylic acid chain, wherein the at least one carbon is not in the terminal position. As used herein, the term "terminal position," refers to the carbon on the carbon backbone chain of a percarboxylic acid that is furthest from the percarboxyl group.

The term "threshold agent" refers to a compound that inhibits crystallization of water hardness ions from solution, but that need not form a specific complex with the water hardness ion. Threshold agents include but are not limited to a polyacrylate, a polymethacrylate, an olefin/maleic copolymer, and the like.

As used herein, the term "waters" includes fresh water, sea water, produced water, brackish water and water used in oil and gas production systems, or transport waters. Transport waters include e.g., as found in flumes, pipe transports, water stored in pipelines, tanks or other water holding containers, and the like. The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc. The, the term PPM refers to parts per million.

The methods, systems, apparatuses, and compositions of the present invention may comprise, consist essentially of, or consist of the components and ingredients of the present invention as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

Methods of Cleaning Membranes

The present invention comprises peroxyformic acid compositions which can be used as a cleaning composition, namely an antimicrobial cleaning composition, a booster or as part of an alkaline, acid and/or enzymatic cleaning composition, a combination of other peroxy acid and/or oxidizing compositions, and methods of use of the same. As referred to herein, the removing of microorganisms, biofilm and mineral deposits refers to the reduction in microorganisms, biofilm and mineral deposits on a membrane surface, the disbursement of microorganisms, biofilm and mineral deposits on a membrane surface, and/or the inactivating of microorganisms, biofilm and mineral deposits on a membrane surface.

In an aspect, the peroxyformic acid compositions are applied to or contact a membrane in need of removing microbial growth and mineral deposits. Membranes are utilized for a variety of separation methods to convert a mixture of a substance(s) into distinct mixtures, at least one of which is enriched in one or more of the mixture's constituents. The membranes that can be treated according to the invention include any membranes that are designed for periodic cleaning, and are often utilized in various applications requiring separation by filtration. Exemplary industries that utilize membranes that can be treated according to the invention include the energy industry. Energy industry uses membranes for desalination, sulfate removal and contaminant removal. Additional uses include reverse osmosis (RO) desalination applications.

Membranes that can be treated according to the invention include those provided in the form of spiral wound membranes, plate and frame membranes, tubular membranes, capillary membranes, hollow fiber membranes and the like. In the case of spiral wound membranes, it is expected that the industrial commonly available diameters of 3.8 inch, 6.2 inch, and 8.0 inch can be treated using the methods of the present invention. The membranes can be generally characterized according to the size of the particles being filtered. Four common types of membrane types include microfiltration (MF) membranes, ultrafiltration (UF) membranes, nanofiltration (NF) membranes, and reverse osmosis (RO) membranes.

In an aspect, microfiltration membranes are particularly suited for treatment according to the invention, which employs a separation process in which particles and dissolved macromolecules larger than 0.1 µm do not pass through the membrane, and which may be pressure driven. In a further aspect, microfiltration membranes may have a pore size range from about 0.05 to about 1 µm. In a further aspect, microfiltration membranes target particular material and contaminants such as bacteria and suspended solids.

In an aspect, ultrafiltration (UF) membranes are particularly suited for treatment according to the invention. Ultrafiltration is a process of filtration in which hydrostatic pressure forces a filtrate liquid against a semipermeable membrane, suspended solids and solutes of high molecular weight are retained, while water and low molecular weight solutes pass through the membrane, it is used in industry and research for purifying and concentrating macromolecular ($10^3$-$10^6$ Da) solutions. It may be applied in cross-flow or dead-end mode and separation in ultrafiltration may undergo concentration polarization. The exact metes and bounds and protocols for applying and categorizing ultrafiltration are set forth in the scientific reference: Ultrafiltration and Microfiltration Handbook, Second Edition, by Munir Cheryan, Published by CRC Press LLC, (1998), which is herein incorporated by reference. In a further aspect, ultrafiltration membranes may have a pore size range from about 0.005 to about 0.5 µm. In a further aspect, ultrafiltration membranes target particular material and contaminants such as bacteria and suspended solids, plus humic acids and some viruses.

In an aspect, nanofiltration membranes are particularly suited for treatment according to the invention, which employs a separation process in which particles and dissolved macromolecules larger than 1 nm do not pass through the membrane, and which may be pressure driven. In a further aspect, nanofiltration membranes may have a pore size range from about 0.0005 to about 0.01 µm. In a further aspect, nanofiltration membranes target contaminants such as viruses, bacteria, and suspended solids and further target particular materials including dissolved metals and salts.

In an aspect, reverse osmosis (RO) membranes are particularly suited for treatment according to the invention. Reverse osmosis is a water purification technology that uses a hydrostatic force (a thermodynamic parameter) to overcome osmotic pressure (a colligative property) in the water to remove one or more unwanted items from the water, RO may be a membrane based separation process, wherein the osmotic pressure is overcome by the hydrostatic force, it may be driven by chemical potential, RO may be pressure driven, RO can remove many types of molecules and ions from solutions and is used in both industrial processes and in producing potable water, in a pressurized RO process the solute is retained on the pressurized side of the membrane and the pure solvent is allowed to pass to the other side, to be "selective," an RO membrane may be sized to not allow large molecules or ions through the pores (holes), and often only allows smaller components of the solution (such as the solvent) to pass freely, in some cases dissolved molecules larger than 0.5 nm do not pass through membrane. In a further aspect, RO membranes may have a pore size range from about 0.0001 to about 0.001 µm. In a further aspect, reverse osmosis membranes target contaminants such as monovalent ions, multivalent ions, viruses, bacteria, and suspended solids and further target particular materials including smaller dissolved metals and salts.

Because of the pore sizes, each membrane process operates at an optimal pressure. Microfiltration membrane systems generally operate at pressures less than about 30 psig. Ultrafiltration membrane systems generally operate at pressures of about 15-150 psig. Nanofiltration membrane systems generally operate at pressures of about 75-500 psig. Reverse osmosis membrane systems generally operate at pressures of about 200-2000 psig. Membranes can be formed from a variety of materials that are commonly used to form membranes including cellulose acetate, polyamide, polysulfone, vinylidene fluoride, acrylonitrile, stainless steel, ceramic, etc. These various membrane chemical types and other materials of construction may have specific pH, oxidant, solvent, chemical compatibility restrictions, and/or pressure limitations.

Membranes may comprise and/or consist of various polymeric components, including for example, cellulose, cellulose acetate, cellulose tri-acetate, nitrocellulose, polysulfone, polyethersulfone, fully aromatic polyamide, polyvinylidene fluoride, polytetrafluoroethylene, polyacrylnitrile, polypropylene, carbon, an organic membrane materials, such as alpha-aluminum oxide or zirconium oxide, and may include not further specified backing material. Membranes may further or in the alternative comprise and/or consist of ceramic and stainless steel. Additional suitable materials are disclosed in U.S. Pat. No. 7,871,521, which is incorporated by reference in its entirety. The methods of treating a membrane with the peroxyformic acid compositions can include a plurality of steps. A first step can be referred to as a product removal step or displacement where product (e.g. whey, milk, etc.) is removed from the filtration system. The product can be effectively recovered and used as opposed to discharging as plant effluent. In general, the product removal step can be characterized as an exchange step where water, gas, or multiple phase flow displaces the product from the membrane system. The product removal step can last as long as it takes to remove and recover product from the filtration system. In general, it is expected that the product removal step will take at least a couple minutes for most filtration systems.

The dosing of the peroxyformic acid compositions for contacting the membrane is for a sufficient amount of time to contact microorganisms and/or mineral deposits on the membrane. In an aspect, the peroxyformic acid compositions contacts the membrane for at least 15 minutes to 15 hours, for at least 30 minutes to 10 hours, for at least 30 minutes to 5 hours, for at least 30 minutes to 4 hours, or any range of time there between. In an aspect, the dosing of the peroxyformic acid (and optionally other peroxy acids and/or oxidizing chemistries) at lower concentrations for treatment according to the invention is suitable for a longer contact time and further beneficially results in microbial reduction without causing damage to the membrane. In an aspect, the intermittent dosing of the peroxyformic acid compositions provides cleaning at intervals which prevent the build up of microorganisms and/or mineral deposits on the membrane. The dosing can be provided on a daily, bi-weekly, weekly or other interval to ensure dosing at a frequency sufficient to prevent the build up of microorganisms and/or mineral deposits on the membrane.

In an aspect, the peroxyformic acid compositions contact the membranes in a use solution of from about 0.00001% to about 0.1% active peroxyformic acid, from about 0.00005% to about 0.1% active peroxyformic acid, 0.0005% to about 0.1% active peroxyformic acid, 0.005% to about 0.1% active peroxyformic acid, from about 0.01% to about 0.1% active peroxyformic acid, or from about 0.025% to about 0.05% active peroxyformic acid.

In an aspect, the peroxyformic acid compositions contact the membranes at an actives concentration from about 0.5 ppm to about 300 ppm, from about 0.5 ppm to about 200 ppm, from about 1 ppm to about 100 ppm, from about 50 ppm to about 100 ppm, or from about 70 ppm to about 100 ppm active peroxyformic acid.

The peroxyformic acid and the membrane can be contacted to form a treated target composition comprising any suitable concentration of said peroxyformic acid, e.g., at least about 1 ppm, at least about 10 ppm at least about 100 ppm, or preferably from about 1-1,000 ppm of peroxyformic acid. The composition used in the present methods can retain any suitable concentration or percentage of the peroxyformic acid activity for any suitable time after the treated target composition is formed. In some embodiments, the composition used in the present methods retains at least about 50%, 55%, 60%, 65%, 70%, 75%, 80%, 85% or 90% of the initial peroxyformic acid activity for any suitable time after the treated target composition is formed. In other embodiments, the composition used in the present methods retains at least about 60% of the initial peroxyformic acid activity for at least 1, 2, 3, 4, 5, 6, 7, 8, 9, 10, 11, 12, 13, 14, 15, 20, 25, 30 minutes, 1 hour, or 2 hours after the treated target composition is formed.

In an aspect, the temperature of the membrane treatment may be between about 4° C. to 60° C., between about 4° C. to 50° C., between about 4° C. to 40° C., or any range of there between. In an aspect, the temperature of the membrane treatment may be ambient temperatures, such as from 4° C. to 30° C. In a further aspect of the invention, and without wishing to be limited to a particular theory, the temperature of the membrane treatment is selected so as to provide desirable chemical kinetics, avoid precipitation of compositions, and to account for geographic and/or environmental concerns.

In an aspect, the pressure of the membrane treatment is selected so that the pressure drop from feed to concentrate is compensated for. In a still further aspect, the pressure is selected to that little to no permeate is produced. In a further aspect, and without wishing to be limited to a particular theory, the pressure selected is low enough that redeposition of dirt and/or other fouling material on the membrane is minimized. In an aspect, the feed pressure may be between about 20 psig and 60 psig.

Beneficially, the methods of treating the membrane do not negatively interfere with the compatibility of the membrane, as may be measured by the flux through the membrane, i.e. the flow rate of water or a solution processed through membrane. In a beneficial aspect, the method of treating the membrane does not result in any negative impact on performance, such as may be determined by flux, pressure or other measurements understood by those skilled in the art. Additionally, the methods of treating a membrane according to the present invention does not produce negative or detrimental chemical reactions, such as chlorine species, with the membrane material that would otherwise create chemical incompatibility.

In an aspect, the peroxyformic acid can treat a membrane for periods of at least one year, at least two years, or at least three years without damaging the membrane surface in a way that interferes with flow.

In an aspect of the invention, the methods of treating the membrane with a peroxyformic acid composition replace the need for or reduce the amount of the conventional biocide employed in energy services applications, namely 2,2-dibromo-3-nitrilopropionamide (DBNPA). The peroxyformic acid composition used in place of the DBNPA or other conventional biocides beneficially removes the need to hold treated water in a sump or other retention step in order to treat the water before it is overboarded in offshore applications of use. The use of peroxyformic acid compositions does not require further treatment and/or time to remove the biocide due to the short half-life of the peroxyformic acid.

The methods of treating the membranes according to the invention provide broad antimicrobial efficacy. In a particular aspect, the methods of treating the membranes according to the invention provide biofilm antimicrobial and biocidal efficacy. Exemplary microorganisms susceptible to the peracid compositions of the invention include, gram positive bacteria (e.g., *Staphylococcus aureus, Bacillus* species (sp.) like *Bacillus subtilis*, Clostridia sp.), gram negative bacteria (e.g., *Escherichia coli, Pseudomonas* sp., *Klebsiella pneumoniae, Legionella pneumophila, Enterobacter* sp., *Serratia* sp., *Desulfovibrio* sp., and *Desulfotomaculum* sp. *Desulfo-*

*vibio* sp.), planktonic microbes, sessile microbes, yeasts (e.g., *Saccharomyces cerevisiae* and *Candida albicans*), molds (e.g., *Aspergillus niger, Cephalosporium acremonium, Penicillium notatum,* and *Aureobasidium pullulans*), filamentous fungi (e.g., *Aspergillus niger* and *Cladosporium resinae*), algae (e.g., *Chlorella vulgaris, Euglena gracilis,* and *Selenastrum capricornutum*), and other analogous microorganisms and unicellular organisms (e.g., phytoplankton and protozoa). Other exemplary microorganisms susceptible to the peracid compositions of the invention include the exemplary microorganisms disclosed in U.S. patent application US 2010/0160449, e.g., the sulfur- or sulfate-reducing bacteria, such as *Desulfovibrio* and *Desulfotomaculum* species.

The methods of treating the membranes according to the invention provide mineral scale removal and removal of mineral buildup conventionally found on membranes. In a particular aspects, the methods of treating the membranes according to the invention provide scale and mineral removal and prevention of buildup or accumulation. Mineral scales are soluble salts that precipitate out as crystalline mineral scales within a system, such as filtration systems employing membranes. Examples of mineral scales include calcium carbonate, calcium sulfate, calcium phosphate, barium sulfate, strontium sulfate, iron hydroxide, iron sulfide, silicone dioxide (silica), calcium oxalate, etc.

Another step often used can be referred to as a pre-rinse step. In general, water and/or an alkaline solution can be run through the filtration system to remove soils. It should be understood that a large-scale filtration system refers to an industrial system having at least about 10 membrane vessels, at least about 40 membranes, and a total membrane area of at least about 200 m$^2$. Industrial filtration systems for use in dairy and brewery applications often include about 10 to about 200 membrane vessels, about 40 to about 1,000 membranes, and a total membrane area of about 200 m$^2$ to about 10,000 m$^2$.

In an aspect, the methods of treating the membrane with the peroxyformic acid compositions can further comprise additional treatment cycles including an acidic treatment, an alkaline treatment, an enzymatic treatment and/or a neutral treatment either before or after the peroxyformic acid composition contacts the membrane.

In an alternative aspect, the methods of treating the membrane with the peroxyformic acid compositions can exclude any additional treatment cycles including an acidic treatment, an alkaline treatment, an enzymatic treatment and/or a neutral treatment either before or after the peroxyformic acid composition contacts the membrane.

In an aspect, an alkaline treatment employs an alkaline use solution to contact the membrane at the same time, and/or before, and/or after the peroxyformic acid composition has been applied to the surface. Exemplary alkaline sources suitable for use with the methods of the present invention include, but are not limited to, basic salts, amines, alkanol amines, carbonates and silicates. Other exemplary alkaline sources for use with the methods of the present invention include NaOH (sodium hydroxide), KOH (potassium hydroxide), TEA (triethanol amine), DEA (diethanol amine), MEA (monoethanolamine), sodium carbonate, and morpholine, sodium metasilicate and potassium silicate. The alkaline source selected is compatible with the surface to be cleaned. In some embodiments, the alkaline override use solution includes an activator complex. In other embodiments, an activator complex is applied to the surface prior to the application of an alkaline override use solution. The alkaline override use solution selected is dependent on a variety of factors, including, but not limited to, the type of soil to be removed, and the surface from which the soil is removed.

In an aspect, an acidic treatment employs an acidic use solution to contact the membrane at the same time, and/or before, and/or after the peroxyformic acid composition has been applied to the surface. Exemplary acid sources suitable for use with the methods of the present invention include, but are not limited to, mineral acids (e.g., phosphoric acid, nitric acid, sulfuric acid) and organic acids (e.g., lactic acid, acetic acid, hydroxyacetic acid, citric acid, glutamic acid, glutaric acid, methane sulfonic acid, acid phosphonates (e.g., HEDP), and gluconic acid). In some embodiments, the ideal additional acidic component provides good chelation once neutralized by the alkaline override use solution. In some embodiments, the additional acidic component present in the active oxygen use solution includes a carboxylic acid. Generally, carboxylic acids have the formula R—COOH wherein the R may represent any number of different groups including aliphatic groups, alicyclic groups, aromatic groups, heterocyclic groups, all of which may be saturated or unsaturated as well as substituted or unsubstituted. Carboxylic acids for use with the methods of the present invention may include those having one, two, three, or more carboxyl groups.

In an aspect, membranes treated with the peroxyformic acid compositions according to the invention do not decrease the lifespan of the membrane in comparison to a membrane treated with a conventional acidic and alkaline cleaning process. In an aspect, membranes treated according to the invention are suitable for use for at least 6 months to a year, at least 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months, at least 23 months, or at least 24 months. One skilled in the art ascertains that the lifespan of a membrane is impacted by various factors including process methods, pressure, pH, temperature, etc.

Membrane Filtration Cleaning Compositions

In one aspect, the present invention employs peroxyformic acid compositions produced in situ or at a point of use for the treatment of membranes according to the invention comprising contacting formic acid with hydrogen peroxide to form a resulting aqueous composition that comprises a peracid that comprises peroxyformic acid, wherein before said contacting, the ratio between the concentration of said formic acid (w/v) and the concentration of said hydrogen peroxide (w/v) is about 2 or higher, and the ratio between the concentration of said peracid (w/w) and the concentration of hydrogen peroxide (w/w) in said formed resulting aqueous composition reaches about 2 or higher within preferably about 1 hour, or preferably within about 10 minutes of said contacting.

In a further aspect, the present invention employs a combination of acids produced in situ or at the point of use for the treatment of membranes according to the invention. In one embodiment of the invention, the combination of acids comprises for example, formic acid and acetic acid, which is then contacted with hydrogen peroxide to form a resulting aqueous composition that comprises a peracid composition that comprises peroxyformic acid and peroxyacetic acid, wherein the ratio between the concentration of said formic acid and acetic acid and the concentration of said hydrogen peroxide (w/v) is about 2 or higher, and the ratio between the concentration of said peracid (w/w) and the concentration of hydrogen peroxide (w/w) in said formed resulting aqueous composition reaches about 2 or higher within preferably about 1 hour, or preferably within about 10 minutes of said contacting.

The formic acid used in the present methods can be provided in any suitable way. In some embodiments, before the contacting step, the formic acid can be provided in a composition that comprises formic acid, e.g., an aqueous solution that comprises formic acid. In other embodiments, before the contacting step, the formic acid can be provided in a composition that comprises a substance that generates formic acid upon contact with an aqueous composition. Any suitable substance that generates formic acid can be used in the present methods. The substance can be a salt of formate, e.g., a sodium or ammonium salt of formate, or an ester of formate. Exemplary esters of formate include glycerol formates, ethylene glycol formates, pentaerythritol formates, mannitol formates, propylene glycol formates, sorbitol formates and sugar formates. Exemplary sugar formates include sucrose formates, dextrin formates, maltodextrin formates, and starch formates. In some embodiments the formates may be provided in a solid composition, such as a starch formate.

The hydrogen peroxide used in the present methods can be provided in any suitable way. In some embodiments, before the contacting step, the hydrogen peroxide can be provided in a composition that comprises hydrogen peroxide, e.g., an aqueous solution that comprises hydrogen peroxide. In other embodiments, before the contacting step, the hydrogen peroxide can be provided in a composition that comprises a substance that generates hydrogen peroxide upon contact with an aqueous composition. Any suitable substance that generates hydrogen peroxide can be sued in the present methods. The substance can comprise a precursor of hydrogen peroxide. Any suitable precursor of hydrogen peroxide can be used in the present methods. For example, the precursor of hydrogen peroxide can be sodium percarbonate, sodium perborate, urea hydrogen peroxide, or PVP-hydrogen peroxide.

In some embodiments, formic acid provided in a first aqueous composition is contacted with hydrogen peroxide provided in a second aqueous composition to form peroxyformic acid and/or mixed peroxyacids and/or acids in the resulting aqueous composition. In other embodiments, formic acid provided in a first aqueous composition is contacted with a substance that generates hydrogen peroxide upon contact with an aqueous composition provided in a second solid composition to form peroxyformic acid in the resulting aqueous composition. In still other embodiments, a substance that generates formic acid upon contact with an aqueous composition provided in a first solid composition is contacted with hydrogen peroxide provided in a second aqueous composition to form peroxyformic acid in the resulting aqueous composition. In yet other embodiments, a substance that generates formic acid upon contact with an aqueous composition provided in a first solid composition and a substance that generates hydrogen peroxide upon contact with an aqueous composition provided in a second solid composition are contacted with a third aqueous composition to form peroxyformic acid in the resulting aqueous composition. In yet other embodiments, a substance that generates formic acid upon contact with an aqueous composition and a substance that generates hydrogen peroxide upon contact with an aqueous composition are provided in a first solid composition, and the first solid composition is contacted with a second aqueous composition to form peroxyformic acid in the resulting aqueous composition.

The resulting aqueous composition that comprises peroxyformic acid can be any suitable types of aqueous compositions. For example, the resulting aqueous composition can be an aqueous solution. In another example, the resulting aqueous composition can be an aqueous suspension.

Before the contacting step, the ratio between the concentration of the formic acid (w/v) and the concentration of the hydrogen peroxide (w/v) can be in any suitable range. In some embodiments, before the contacting, the ratio between the concentration of the formic acid (w/v) and the concentration of the hydrogen peroxide (w/v) can be from about 2 to about 100, e.g., about 2-3, 3-4, 4-5, 5-6, 6-7, 7-8, 8-9, 9-10, 10-15, 15-20, 20-25, 25-30, 30-35, 35-40, 40-45 or 45-50 or greater from about 50-100.

The ratio between the concentration of the peracid (w/w) and the concentration of hydrogen peroxide (w/w) in the formed aqueous composition can reach any suitable range. In some embodiments, the ratio between the concentration of the peracid (w/w) and the concentration of hydrogen peroxide (w/w) in the formed aqueous composition can reach, within about 4 hours, or preferably 2 hours of the contacting, from about 2 to about 1,500, e.g., about 2-3, 3-4, 4-5, 5-6, 6-7, 7-8, 8-9, 9-10, 10-15, 15-20, 20-25, 25-30, 30-35, 35-40, 40-45, 45-50, 50-60, 60-70, 70-80, 80-90, 90-100, 100-200, 200-300, 300-400, 400-500, 500-600, 600-700, 700-800, 800-900, 900-1,000, 1,000-1,100, 1,100-1,200, 1,200-1,300, 1,300-1,400, or 1,400-1,500. In other embodiments, the ratio between the concentration of the peracid (w/w) and the concentration of hydrogen peroxide (w/w) in the formed aqueous composition reaches at least about 10 within about 30 minutes of the contacting, preferably at least about 10-40 within about 30 minutes of the contacting.

The formed aqueous composition can comprise any suitable concentration of hydrogen peroxide. In some embodiments, the formed aqueous composition can comprise about 5% (w/w) or less hydrogen peroxide, e.g., about 5% (w/w), 4.5% (w/w), 4% (w/w), 3.5% (w/w), 3% (w/w), 2.5% (w/w), 2% (w/w), 1.5% (w/w), 1% (w/w), 0.9% (w/w), 0.8% (w/w), 0.7% (w/w), 0.6% (w/w), 0.5% (w/w), 0.4% (w/w), 0.3% (w/w), 0.2% (w/w), 0.1% (w/w), 0.05% (w/w), 0.01% (w/w), 0.005% (w/w), or 0.001% (w/w) of hydrogen peroxide. In other embodiments, the formed aqueous composition reaches about 2% (w/w) or less hydrogen peroxide within about 1 hour, or preferably within about 10 minutes of the contacting. In still other embodiments, the formed aqueous composition reaches about 1% (w/w) or less hydrogen peroxide within about 1 hour of the contacting. In yet other embodiments, the formed aqueous composition reaches about 0% (w/w) to about 0.001% (w/w) hydrogen peroxide and maintains about 0% (w/w) to about 0.001% (w/w) hydrogen peroxide for about 1 hour.

In many aspects of the invention, a low hydrogen peroxide containing peroxyformic acid is desirable and unexpectedly provides benefits in treating membranes. In an embodiment, a low hydrogen peroxide containing peroxyformic acid does not cause damage to membranes, including under seawater treatment environments and overcomes a significant limitation of the state of the art. In a preferred aspect, the peroxyformic acid compositions include non-equilibrium ratios of peroxyformic acid to hydrogen peroxide. In an aspect, the ratio of peroxyformic acid to hydrogen peroxide is at least 5:1, at least 10:1, at least 15:1, at least 20:1, at least 25:1, at least 30:1, at least 35:1, or at least 40:1. This is distinct from conventional peroxycarboxylic acids, such as peroxyacetic acid having a ratio of peroxycarboxylic acid to hydrogen peroxide of about 1:1 to about 1.5:1.

The formic acid and the hydrogen peroxide can be contacted in the absence of a $C_2$-$C_{22}$ carboxylic acid and/or a $C_2$-$C_{22}$ percarboxylic acid and the peracid in the formed aqueous composition comprises peroxyformic acid only.

The formic acid and hydrogen peroxide can be contacted in the presence of a $C_2$-$C_{22}$ carboxylic acid and the peracid in the formed aqueous composition comprises peroxyformic acid and the $C_2$-$C_{22}$ percarboxylic acid. Any suitable $C_2$-$C_{22}$ carboxylic acid can be used in the present methods. In some embodiments, the $C_2$-$C_{22}$ carboxylic acid is acetic acid, octanoic acid and/or sulfonated oleic acid, and the peracid in the formed aqueous composition comprises peroxyformic acid and one or more of peroxyacetic acid, peroxyoctanoic acid and peroxysulfonated oleic acid.

The present methods can be conducted at any suitable temperature. In some embodiments, the present methods can be conducted at a temperature ranging from about −2° C. to about 70° C., about 10° C. to about 70° C., e.g., about 10° C.-15° C., 15° C.-20° C., 20° C.-25° C., 25° C.-30° C., 30° C.-35° C., 35° C.-40° C., 40° C.-45° C., 45° C.-50° C., 50° C.-55° C., 55° C.-60° C., 60° C.-65° C., or 65° C.-70° C. In other embodiments, the present methods can be conducted under ambient conditions. In still other embodiments, the present methods can be conducted under heating, e.g., at a temperature ranging from about 30° C.-35° C., 35° C.-40° C., 40° C.-45° C., 45° C.-50° C., 50° C.-55° C., 55° C.-60° C., 60° C.-65° C., or 65° C.-70° C.

The present methods can be conducted in the presence of a catalyst. Any suitable catalyst can be used in the present methods. In some embodiments, the catalyst can be a mineral acid, e.g., sulfuric acid, nitric acid, phosphoric acid, pyrophosphoric acid, polyphosphoric acid, or organic acids, such as methanesulfonic acid, xylene sulfonic acid, toluene sulfonic acid, phosphonic acids such as 1-hydroxyethane 1,1-diphosphonic acid (HEDP)

The present methods can be conducted in the presence of a cation acid exchange resin system. Any suitable cation acid exchange resin system can be used in the present methods. In some embodiments, the cation acid exchange resin system is a strong cation acid exchange resin system. In other embodiments, the acid exchange resin system is sulfonic acid exchange resin, e.g., commercially-available as Dowex M-31 or Nafion.

The formic acid provided in a first aqueous composition can be contacted with the hydrogen peroxide provided in a second aqueous composition that also comprises peroxyacetic acid to form a resulting aqueous composition that comprises a total peracid that comprises peroxyformic acid and peroxyacetic acid. Before the contacting step, the ratio between the concentration of the formic acid (w/v) and the concentration of the hydrogen peroxide (w/v) can be at any suitable range. The ratio between the concentration of total peracid (w/w) and the concentration of hydrogen peroxide (w/w) in the resulting aqueous composition can also reach any suitable range. In some embodiments, before the contacting, the ratio between the concentration of the formic acid (w/v) and the concentration of the hydrogen peroxide (w/v) can be about 5 or higher and the ratio between the concentration of total peracid (w/w) and the concentration of hydrogen peroxide (w/w) in the resulting aqueous composition reaches at least about 5 within about 2 minutes of the contacting. In other embodiments, the ratio between the concentration of total peracid (w/w) and the concentration of hydrogen peroxide (w/w) in the resulting aqueous composition can reach at least about 10 within about 20 minutes of the contacting. In yet other embodiments, before the contacting, the ratio between the concentration of the formic acid (w/v) and the concentration of the hydrogen peroxide (w/v) can be about 20 or higher and the ratio between the concentration of total peracid (w/w) and the concentration of hydrogen peroxide (w/w) in the resulting aqueous composition can reach at least about 10 within at least about 1 minute of the contacting. The concentration of hydrogen peroxide (w/w) in the resulting aqueous composition can reach any suitable concentration. In some embodiments, the concentration of hydrogen peroxide (w/w) in the resulting aqueous composition can reach about 0% (w/w) to about 0.001% (w/w) hydrogen peroxide within at least about 4 hours, or preferably 2 hours of the contacting. In other embodiments, the concentration of hydrogen peroxide (w/w) in the resulting aqueous composition can remain at about 0% (w/w) to about 0.001% (w/w) for least 1 hour. In other embodiments, the concentration of hydrogen peroxide in the resulting aqueous composition can remain at about 0% to about 0.1% for least 10 min.

The resulting aqueous composition can comprise a stabilizing agent for the peracid. Any suitable stabilizing agents can be used in the present methods. Exemplary stabilizing agents include a phosphonate salt(s) and/or a heterocyclic dicarboxylic acid, e.g., dipicolinic acid.

The present methods can further comprise a step of reducing the concentration of the hydrogen peroxide in the resulting aqueous composition. The concentration of the hydrogen peroxide in the resulting aqueous composition can be reduced using any suitable methods. For example, the concentration of the hydrogen peroxide in the resulting aqueous composition can be reduced using a catalase or a peroxidase.

The resulting aqueous composition can comprise any suitable concentration of peroxyformic acid. In some embodiments, the resulting aqueous composition comprises from about 0.00001% (w/w) to about 20% (w/w) peroxyformic acid, e.g., about 0.0001%-0.005% (w/w), 0.0005%-0.01% (w/w), 0.001%-0.05% (w/w), 0.005%-0.1% (w/w), 0.01%-0.5% (w/w), 0.05%-1% (w/w), 1%-2% (w/w), 2%-3% (w/w), 3%-4% (w/w), 4%-5% (w/w), 5%-6% (w/w), 6%-7% (w/w), 7%-8% (w/w), 8%-9% (w/w), 9%-10% (w/w), 10%-11% (w/w), 11%-12% (w/w), 12%-13% (w/w), 13%-14% (w/w), 14%-15% (w/w), 15%-16% (w/w), 16%-17% (w/w), 17%-18% (w/w), 18%-19% (w/w), or 19%-20% (w/w) peroxyformic acid.

The present methods can be used to generate peroxyformic acid in any suitable manner or at any suitable location. In some embodiments, the present methods can be used to generate peroxyformic acid in situ for the application of the formed peroxyformic acid.

The peroxyformic acid formed using the present methods (present composition) can further comprise other percarboxylic acids. A peracid includes any compound of the formula R—(COOOH)$_n$, in which R can be hydrogen, alkyl, alkenyl, alkyne, acylic, alicyclic group, aryl, heteroaryl, or heterocyclic group, and n is 1, 2, or 3, and named by prefixing the parent acid with peroxy. Preferably R includes hydrogen, alkyl, or alkenyl. The terms "alkyl," "alkenyl," "alkyne," "acylic," "alicyclic group," "aryl," "heteroaryl," and "heterocyclic group" are as defined herein. Various embodiments of the invention referring to peroxyformic acid compositions and/or peroxyformic acid solutions are further understood to optionally comprise additional percarboxylic acids. As used herein, the term "peracid" may also be referred to as a "percarboxylic acid" or "peroxyacid." Sulfoperoxycarboxylic acids, sulfonated peracids and sulfonated peroxycarboxylic acids are also included within the term "peracid" as used herein. The terms "sulfoperoxycarboxylic acid," "sulfonated peracid," or "sulfonated peroxycarboxylic acid" refers to the peroxycarboxylic acid form of a sulfonated carboxylic acid as disclosed in U.S. Patent Publication Nos. 2010/0021557, 2010/0048730 and 2012/0052134 which are incorporated herein by reference in their entireties. A peracid refers to an acid having the hydrogen of the hydroxyl group in carboxylic acid replaced by a hydroxy group. Oxidizing peracids may also be referred to herein as peroxycarboxylic acids.

In other embodiments, a mixed peracid is employed, such as a peroxycarboxylic acid including at least one peroxycarboxylic acid of limited water solubility in which R includes alkyl of 5-22 carbon atoms and at least one water-soluble peroxycarboxylic acid in which R includes alkyl of 1-4 carbon atoms. For example, in one embodiment, a peroxycarboxylic acid includes peroxyacetic acid and at least one other peroxycarboxylic acid such as those named above. Preferably a composition of the invention includes peroxyformic acid, peroxyacetic acid and/or peroxyoctanoic acid. Other combinations of mixed peracids are well suited for use in the current invention. Advantageously, a combination of peroxycarboxylic acids provides a composition with desirable antimicrobial activity in the presence of high organic soil loads. The mixed peroxycarboxylic acid compositions often provide synergistic micro efficacy. Accordingly, compositions of the invention can include a peroxycarboxylic acid, or mixtures thereof.

Water

The peroxyformic acid compositions according to the invention may comprise water in amounts that vary depending upon techniques for processing the composition. Water provides a medium which dissolves, suspends, or carries the other components of the composition. Water can also function to deliver and wet the composition of the invention on an object.

In some embodiments, water makes up a large portion of the composition of the invention and may be the balance of the composition apart from peroxyformic acid composition. The water amount and type will depend upon the nature of the composition as a whole, the environmental storage, and method of application including concentration composition, form of the composition, and intended method of delivery, among other factors. Notably the carrier should be chosen and used at a concentration which does not inhibit the efficacy of the functional components in the composition of the invention for the intended use.

Additional Peroxy Acids

The peroxyformic acid compositions according to the invention may comprise an additional peroxyacid. Any suitable $C_1$-$C_{22}$ percarboxylic acid can be used in the present compositions. In some embodiments, the $C_1$-$C_{22}$ percarboxylic acid is a $C_2$-$C_{20}$ percarboxylic acid. In other embodiments, the $C_1$-$C_{22}$ percarboxylic is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ percarboxylic acid. In still other embodiments, the additional $C_1$-$C_{22}$ percarboxylic acid comprises peroxyacetic acid, peroxyoctanoic acid and/or peroxysulfonated oleic acid.

The additional percarboxylic acid can be added to the peroxyformic acid in any suitable concentration. In some embodiments, the resulting aqueous composition comprises from about 0.00001% (w/w) to about 20% (w/w) peroxyformic acid, e.g., about 0.0001%-0.005% (w/w), 0.0005%-0.01% (w/w), 0.001%-0.05% (w/w), 0.005%-0.1% (w/w), 0.01%-0.5% (w/w), 0.05%-1% (w/w), 1%-2% (w/w), 2%-3% (w/w), 3%-4% (w/w), 4%-5% (w/w), 5%-6% (w/w), 6%-7% (w/w), 7%-8% (w/w), 8%-9% (w/w), 9%-10% (w/w), 10%-11% (w/w), 11%-12% (w/w), 12%-13% (w/w), 13%-14% (w/w), 14%-15% (w/w), 15%-16% (w/w), 16%-17% (w/w), 17%-18% (w/w), 18%-19% (w/w), or 19%-20% (w/w).

Additional Functional Ingredients

The components of the peroxyformic acid compositions can further be combined with various functional components suitable for use in membrane treatment. In some embodiments, the peroxyformic acid compositions make up a large amount, or even substantially all of the treatment composition for the membranes as disclosed herein. For example, in some embodiments few or no additional functional ingredients are disposed therein.

In other embodiments, additional functional ingredients may be included in the compositions. The functional ingredients provide desired properties and functionalities to the compositions. For the purpose of this application, the term "functional ingredient" includes a material that when dispersed or dissolved in a use and/or concentrate solution, such as an aqueous solution, provides a beneficial property in a particular use. Some particular examples of functional materials are discussed in more detail below, although the particular materials discussed are given by way of example only, and that a broad variety of other functional ingredients may be used.

In some embodiments, the peroxyformic acid compositions may include surfactants, such as for example nonionic and anionic surfactants, defoaming agents, anti-redeposition agents, bleaching agents, solubility modifiers, dispersants, rinse aids, metal protecting agents, stabilizing agents, corrosion inhibitors, sequestrants and/or chelating agents, wetting agents, water conditioning agents or chelants, enzymes, fragrances and/or dyes, rheology modifiers or thickeners, hydrotropes or couplers, buffers, acids and bases, mineral and organic acids, solvents and the like.

Builders

The present compositions or cleaning use solutions can include a builder. Builders include chelating agents (chelators), sequestering agents (sequestrants), and the like. The builder may act to stabilize the cleaning composition or use solution. Examples of builders include, but are not limited to, phosphonates, phosphates, aminocarboxylates and their derivatives, pyrophosphates, polyphosphates, ethylenediamine and ethylenetriamene derivatives, hydroxyacids, and mono-, di-, and tri-carboxylates and their corresponding acids. Other exemplary builders include aluminosilicates, nitroloacetates and their derivatives, and mixtures thereof. Still other exemplary builders include aminocarboxylates, including salts of ethylenediaminetetraacetic acid (EDTA), hydroxyethylenediaminetetraacetic acid (HEDTA), and diethylenetriaminepentaacetic acid. For a further discussion of chelating agents/sequestrants, see Kirk-Othmer, Encyclopedia of Chemical Technology, Third Edition, volume 5, pages 339-366 and volume 23, pages 319-320, which is incorporated in its entirety. According to an aspect of the invention, preferred builders are water soluble, biodegradable and phosphorus-free. The amount of builder in the cleaning composition or use solution, if present, is typically between about 10 ppm and about 1000 ppm in the cleaning composition or use solution.

Acidulants and Catalysts

Acidulants may be included as additional functional ingredients in a composition according to the invention. In an aspect, a strong mineral acid such as nitric acid, sulfuric acid, phosphoric acid or a stronger organic acid such as methyl sulfonic acid (MSA) can be used. The combined use of a strong mineral acid or stronger organic acid with the peracid composition provides enhanced antimicrobial efficacy. In addition, some strong mineral and organic acids, such as nitric acid, provide a further benefit of reducing the risk of corrosion toward metals contacted by the peracid compositions according to the invention. In some embodiments, the present composition does not comprise a mineral acid or a strong mineral acid.

In an aspect, the methods of forming the peroxyformic acid may be conducted in the presence of a catalyst. Any suitable catalyst can be used in the present methods. In some embodiments, the catalyst can be a mineral or strong organic acid, e.g., sulfuric acid, nitric acid, phosphoric acid, pyrophosphoric acid, polyphosphoric acid. The catalyst may also be an organic acid, e.g., methanesulfonic acid, xylene sulfonic acid, toluene sulfonic acid, phosphonic acid such as HEDP. Such catalysts may be present in peroxyformic acid forming composition in an amount of at least about 0 wt-% to about 10 wt-%, preferably at least about 0.1 wt-% to about 5 wt-%, more preferably from about 1 wt-% to about 5 wt-%.

Acidulants may be employed in amounts sufficient to provide the intended antimicrobial efficacy and/or anticorrosion benefits. Such agents may be present in a use solution in an amount of at least about 0.1 wt-% to about 10 wt-%, preferably at least about 0.1 wt-% to about 5 wt-%, more preferably from about 0.1 wt-% to about 1 wt-%.

Surfactants

The surfactants described hereinabove can be used singly or in combination with the methods of the present invention. In particular, the nonionics and anionics can be used in combination. The semi-polar nonionic, cationic, amphoteric and zwitterionic surfactants can be employed in combination with nonionics or anionics. The above examples are merely specific illustrations of the numerous surfactants which can find application within the scope of this invention. It should be understood that the selection of particular surfactants or combinations of surfactants can be based on a number of factors including compatibility with the membrane at the intended use concentration and the intended environmental conditions including temperature and pH. Accordingly, one should understand that surfactants that may damage a particular membrane during conditions of use should not be used with that membrane. It is expected that the same surfactant, however, may be useful with other types of membranes. In addition, the level and degree of foaming under the conditions of use and in subsequent recovery of the composition can be a factor for selecting particular surfactants and mixtures of surfactants. For example, in certain applications it may be desirable to minimize foaming and, as a result, one would select a surfactant or mixture of surfactants that provides reduced foaming. In addition, it may be desirable to select a surfactant or a mixture of surfactants that exhibits a foam that breaks down relatively quickly so that the composition can be recovered and reused with an acceptable amount of down time. In addition, the surfactant or mixture of surfactants can be selected depending upon the particular soil that is to be removed.

It should be understood that the compositions for use with the methods of the present invention need not include a surfactant or a surfactant mixture, and can include other components. In addition, the compositions can include a surfactant or surfactant mixture in combination with other components. Exemplary additional components that can be provided within the compositions include builders, water conditioning agents, non-aqueous components, adjuvants, carriers, processing aids, enzymes, and pH adjusting agents. When surfactants are included in the peroxyformic acid compositions in a use solution they can be included in an amount of at least about 0.1 wt. % to about 10 wt. %.

Anionic Surfactants

The peroxyformic acid compositions can contain a surfactant component(s) that includes a detersive amount of an anionic surfactant or a mixture of anionic surfactants. Anionic surfactants are desirable in cleaning compositions because of their wetting, detersive properties, and often times good compatibility with membranes. The anionic surfactants that can be used according to the invention include any anionic surfactant available in the cleaning industry. Suitable groups of anionic surfactants include sulfonates and sulfates. Suitable surfactants that can be provided in the anionic surfactant component include alkyl aryl sulfonates, secondary alkane sulfonates, alkyl methyl ester sulfonates, alpha olefin sulfonates, alkyl ether sulfates, alkyl sulfates, and alcohol sulfates. Suitable alkyl aryl sulfonates that can be used in the cleaning composition can have an alkyl group that contains 6 to 24 carbon atoms and the aryl group can be at least one of benzene, toluene, and xylene. A suitable alkyl aryl sulfonate includes linear alkyl benzene sulfonate. A suitable linear alkyl benzene sulfonate includes linear dodecyl benzyl sulfonate that can be provided as an acid that is neutralized to form the sulfonate. Additional suitable alkyl aryl sulfonates include xylene sulfonate. Suitable alkane sulfonates that can be used in the cleaning composition can have an alkane group having 6 to 24 carbon atoms. Suitable alkane sulfonates that can be used include secondary alkane sulfonates. A suitable secondary alkane sulfonate includes sodium C14-C17 secondary alkyl sulfonate. Suitable alkyl methyl ester sulfonates that can be used in the cleaning composition include those having an alkyl group containing 6 to 24 carbon atoms. Suitable alpha olefin sulfonates that can be used in the cleaning composition include those having alpha olefin groups containing 6 to 24 carbon atoms. Suitable alkyl ether sulfates that can be used in the cleaning composition include those having between about 1 and about 10 repeating alkoxy groups, between about 1 and about 5 repeating alkoxy groups. In general, the alkoxy group will contain between about 2 and about 4 carbon atoms. A suitable alkoxy group is ethoxy. A suitable alkyl ether sulfate is sodium lauryl ether ethoxylate sulfate. Suitable alkyl sulfates that can be used in the cleaning composition include those having an alkyl group containing 6 to 24 carbon atoms. Suitable alkyl sulfates include, but are not limited to, sodium lauryl sulfate and sodium lauryl/myristyl sulfate. Suitable alcohol sulfates that can be used in the cleaning composition include those having an alcohol group containing about 6 to about 24 carbon atoms.

Further examples of suitable anionic surfactants are given in "Surface Active Agents and Detergents" (Vol. I and II by Schwartz, Perry and Berch). A variety of such surfactants are also generally disclosed in U.S. Pat. No. 3,929,678. The disclosures of the above references relating to anionic surfactants are incorporated herein by reference.

Nonionic Surfactants

The peroxyformic acid compositions can contain a surfactant component(s) that includes a detersive amount of a nonionic surfactant or a mixture of nonionic surfactants. Nonionic surfactants can be included in the composition to enhance soil removal properties. Nonionic surfactants useful in the invention are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water-soluble compound having the desired degree of balance between hydrophilic and hydrophobic properties.

Nonionic surfactants that can be used in the composition include polyalkylene oxide surfactants (also known as polyoxyalkylene surfactants or polyalkylene glycol surfactants). Suitable polyalkylene oxide surfactants include polyoxypropylene surfactants and polyoxyethylene glycol surfactants. Suitable surfactants of this type are synthetic organic polyoxypropylene (PO)-polyoxyethylene (EO) block copolymers. These surfactants include a di-block polymer comprising an EO block and a PO block, a center block of polyoxypropylene units (PO), and having blocks of polyoxyethylene grafted onto the polyoxypropylene unit or a center block of EO with attached PO blocks. Further, this surfactant can have further blocks of either polyoxyethylene or polyoxypropylene in the molecules. A suitable average molecular weight range of useful surfactants can be about 1,000 to about 40,000 and the weight percent content of ethylene oxide can be about 10-80 wt. %.

Additional nonionic surfactants include alcohol alkoxylates. An suitable alcohol alkoxylate include linear alcohol ethoxylates. Additional alcohol alkoxylates include alkylphenol ethoxylates, branched alcohol ethoxylates, secondary alcohol ethoxylates, castor oil ethoxylates, alkylamine ethoxylates, tallow amine ethoxylates, fatty acid ethoxylates, sorbital oleate ethoxylates, end-capped ethoxylates, or mixtures thereof. Additional nonionic surfactants include amides such as fatty alkanolamides, alkyldiethanolamides, coconut diethanolamide, lauramide diethanolamide, cocoamide diethanolamide, polyethylene glycol cocoamide, oleic diethanolamide, or mixtures thereof. Additional suitable nonionic surfactants include polyalkoxylated aliphatic base, polyalkoxylated amide, glycol esters, glycerol esters, amine oxides, phosphate esters, alcohol phosphate, fatty triglycerides, fatty triglyceride esters, alkyl ether phosphate, alkyl esters, alkyl phenol ethoxylate phosphate esters, alkyl polysaccharides, block copolymers, alkyl glucosides, or mixtures thereof.

Other exemplary nonionic surfactants for use with the methods of the present invention are disclosed in the treatise Nonionic Surfactants, edited by Schick, M. J., Vol. 1 of the Surfactant Science Series, Marcel Dekker, Inc., New York, 1983, the contents of which is incorporated by reference herein. A typical listing of nonionic classes, and species of these surfactants, is also given in U.S. Pat. No. 3,929,678. Further examples are given in "Surface Active Agents and Detergents" (Vol. I and II by Schwartz, Perry and Berch). The disclosures of these references relating to nonionic surfactants are incorporated herein by reference.

Amphoteric Surfactants

Amphoteric surfactants can also be used to provide desired detersive properties. Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge. Suitable amphoteric surfactants include, but are not limited to: sultaines, amphopropionates, amphodipropionates, aminopropionates, aminodipropionates, amphoacetates, amphodiacetates, and amphohydroxypropylsulfonates.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Amphoteric surfactants are subdivided into two major classes. The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Zwitterionic Surfactants

In some embodiments, zwitterionic surfactants are used with the methods of the invention. Zwitterionic surfactants can be thought of as a subset of the amphoteric surfactants. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate. Betaine and sultaine surfactants are exemplary zwitterionic surfactants for use herein.

A typical listing of zwitterionic classes, and species of these surfactants, is given in U.S. Pat. No. 3,929,678. Further examples are given in "Surface Active Agents and Detergents" (Vol. I and II by Schwartz, Perry and Berch). The disclosures of zwitterionic surfactants in the above references are incorporated herein by reference.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The materials used in the following Examples are provided herein:

Various commercially-available stock solutions were employed in formulations (available from various sources) including: methane sulfonic acid (70%), linear alkylbenzene sulphonates (96%), sodium xylene sulfonate (40%), formic acid (85%), and hydrogen peroxide (50%).

POAA: a commercial product containing 5.25 to 6.4% peroxyacetic acid and 25.6 to 29.4% $H_2O_2$.

Exemplary peroxyformic acid compositions employed in the Examples are listed in the Table 1 below:

TABLE 1

| Component | PFA-30-1 (wt %) | PFA-30-2 (wt %) | FA-30-3 (wt %) |
| --- | --- | --- | --- |
| Water | 0.00 | 0.00 | 16.25 |
| MSA (70%) | 3.0 | 3.0 | 3.0 |
| LAS (96%) | 4.93 | 0 | 4.93 |
| Formic acid (85%) | 75.82 | 80.75 | 75.82 |
| $H_2O_2$ (50%) | 16.25 | 16.25 | 0 |
| Total | 100.00 | 100.00 | 100.00 |
| PFA (5 min after mixing) | 10.19% | 9.22% | 0.00% |

The peroxyformic acid compositions shown in Table 1 were made from a two-part system. Part A provided the formic acid and optionally with other ingredients excluding the $H_2O_2$. Part B for the formulations PFA 30-1 and PFA 30-2 provided $H_2O_2$ and optionally with other ingredients excluding the formic acid provided in Part A. On mixing Part A and Part B under ambient conditions, peroxyformic acid (PFA) reached maximum level within 5 min., i.e. the compositions were ready to use. Composition 30-3 is a formic acid composition and not a peroxyformic acid composition.

Accordingly, the peroxyformic acid formed provides a superior biocide against microorganisms, especially spores and biofilms suitable for the uses disclosed herein according to the embodiments of the invention. Moreover, the formic acid in the composition (as demonstrated by Composition 30-3) serves as an efficient proton source in dissolving mineral scale build up on spiral bound membrane elements.

Example 1

The removal of biofilm was tested to determine efficacy of biofilm removal and kill rates of *Pseudomonas aeruginosa*. *Pseudomonas* are well-known as common 'pioneer' bacteria and often tested for biofilm-inhibiting agents' effectiveness. The bacteria are known to excrete polysaccharides and generate biofilm on a variety of surfaces very rapidly (including, for example, membrane filtration elements), as well as commonly demonstrate resistance to various antimicrobial compositions. However, bacteria that exist in a biofilm are phenotypically different from suspended cells of the same genotype; therefore the study of biofilm in the laboratory requires protocols that account for this difference. Laboratory biofilms are engineered in growth reactors designed to produce a specific biofilm type. Altering system parameters correspondingly results in a change in the biofilm.

*Pseudomonas aeruginosa* (ATCC 700888) was the organism used. An isolated colony was aseptically removed from an R2A plate and placed into 100 ml of sterile bacterial liquid growth broth (300 mg/L) and incubated in an environmental shaker at 35° C. for 20-24 hours. Viable bacterial density should equal 108 CFU/ml, and may be checked by serial dilution and plating. *Pseudomonas aeruginosa* were grown in a CDC reactor system for 48 hours at room temperature. See Goeres, D. M., et al., Statistical assessment of a laboratory method for growing biofilms, Microbiology 151:757-762 (2005). Biofilm challenge is approximately 8 logs throughout testing from a 48-hour growth.

Small Koch HFK-131 UF membrane rectangles were prepared by punching out a spiral wound membrane and placing the membrane disk into a plastic rectangle used to serve as "framing material". The membranes were placed into the CDC rod and used for testing.

After the biofilm was developed, the membrane rectangles were removed and placed into a sterile plastic centrifuge tube. Each exemplary composition was pipette into the centrifuge tube in duplicate and exposed to the membrane rectangles for the specified exposure time (5 or 10 minutes) at room temperature. After the specified exposure time the solutions were neutralized in Neutralizer Broth, vortexed, sonicated, serially diluted and plated for plate counts. The average log reduction for each evaluated composition was obtained as follows: peroxyformic acid (Formulations 30-1 and 30-2), untreated control not containing peroxyformic acid (Formulation 30-3), and a commercially-available antimicrobial composition (peroxyacetic acid composition). The results of these experiments are shown in FIG. 1.

As can be seen in FIG. 1, all three exemplary compositions efficiently reduced *Pseudomonas aeruginosa* biofilm at the indicated exposure times. Compositions 30-1 and 30-2 at the concentration of 0.3% (product) provide significant log reduction in (>6.68) at both the 5 and 10-minute exposure times, while the average log reduction for composition 30-3 containing formic acid alone (4.15 at 5 minutes and 3.02 at 10 minutes) has significantly less efficacy against the test microorganism. At least a 3-log reduction in the biofilm organisms is conventionally required as a commercial threshold for biofilm treatments to comply with EPA requirements. Accordingly, the PFA compositions according to the invention provide suitable compositions for membrane treatment.

Accordingly, the peroxyformic acid formed provides a superior biocide against microorganisms, especially spores and biofilms suitable for the uses disclosed herein according to the embodiments of the invention. Moreover, the formic acid in the composition (as demonstrated by Composition 30-3) serves as an efficient proton source and provides benefits to treating the membranes as well.

Example 2

In addition to biofilm disruption during membrane filtration, mineral scale also serves as a significant hindrance which reduces output and decreases the life of the membrane filtration elements. Mitigation of mineral buildup was tested to determine efficacy of the exemplary compositions to solubilize excess minerals.

For these experiments, compositions 30-1 (0.3%), 30-2 (0.3%), and 30-3 (0.3%) were prepared to be tested. Product dilutions were made in DI water and the initial pH of the solution was recorded. The test dilutions are then added to a beaker and stirred at 25° C. Excess amounts of calcium mineral (either phosphate or carbonate solids) were added until the solution was opaque and the amount of mineral added is recorded. The excess mineral is allowed to settle for about 5 minutes and a final pH of the acidic solutions are recorded. The solutions are then filtered and standard ICP-MS methods are used to determine calcium and phosphorus solubility capacity in the various formulations. The results of these experiments are provided in Tables 2A and 2B below which show the ability of the peroxyformic and formic acid compositions to dissolve mineral deposits. As the scale removal capability is dependent on the amount of acid used in the composition, no control data set is provided, instead the compositions 30-1 and 30-2 providing peroxyformic acid are compared with 30-3 providing formic acid.

TABLE 2A

| Formula | ~100 g | $Ca_3(PO_4)_2$ g | Temp | pH (initial) | pH (final) | ICP Ca ppm |
|---|---|---|---|---|---|---|
| PFA-30-1 (0.3%) | 100.6 | 0.50 | 25° C. | 2.53 | 3.60 | 629 |
| PFA-30-2 (0.3%) | 100.1 | 0.50 | 25° C. | 2.52 | 3.94 | 964 |
| Formic Acid 30-3 (0.3%) | 100.2 | 0.50 | 25° C. | 2.49 | 3.61 | 769 |

TABLE 2B

| Formula | ~100 g | $CaCO_3$ g | Temp | pH (initial) | pH (final) | ICP Ca ppm |
|---|---|---|---|---|---|---|
| PFA-30-1 (0.3%) | 100.4 | 0.50 | 25° C. | 2.55 | 5.53 | 943 |
| PFA-30-2 (0.3%) | 100.1 | 0.50 | 25° C. | 2.53 | 5.97 | 1210 |
| Formic Acid 30-3 (0.3%) | 99.9 | 0.50 | 25° C. | 2.49 | 5.44 | 1050 |

All three formulas were very efficient in solubilizing both calcium carbonate and calcium phosphate. In general, an ICP Ca above 400 ppm is considered to display efficient solubilizing capacity which is indicative of the solubilizing of the minerals as required for cleaning a membrane. As can be seen in Tables 2A and 2B, formula 30-2 (0.3%) displays the highest solubility capacity of the formulas tested, while formulas 30-1 and 30-3 show desirable solubility capacity as well. As shown, the peroxyformic acid compositions provide desirable dissolving of mineral scale build up, such as that which is found on membrane elements. The formic acid composition also provides an efficient proton source in dissolving mineral scale build up, such as that which is found on membrane elements. The results confirm that the use of the peroxyformic acid compositions and formic acid compositions are suitable replacements for strong acid cleaning conventionally used in an alternating fashion with an alkaline cleaning step for membranes. Instead, according to embodiments of the invention, the biocidal peroxyformic acid compositions and formic acid compositions can be used in membrane cleaning to replace strong acids which are known to be detrimental (noncompatible) with membranes.

Example 3

It is important that any possible formula used for membrane filtration cleaning be compatible with the membranes and not impact membrane function. To determine the membrane compatibility formula 30-1 (0.5%) was compared to POAA and DI water was used as a negative control.

Membranes are initially rinsed with DI water to remove residual storage buffer and are placed in a 1 gallon jar. The test solutions are added to the 1 gallon jar and placed in an oven at 50° C. for 24 hours. After 24 hours, the test solution is removed and replaced with fresh test solution. The jar is placed back in an oven for 24 hours and this same protocol is repeated 2 more times for a total of 4 days. Based Tables 3A and 3B below 4 days is equivalent to 1.5 years of exposure for daily membrane cleanings.

TABLE 3A

Daily Application

| Wash Time | 10 | Min |
|---|---|---|
| Washes/Week | 7 | Washes |
| Weeks/Year | 52 | Weeks |
| Exposure Time/Year | 3640 | min/year |
|  | 1.5 | Years |
| Total Exposure | 5460 | Minutes |
| Total Exposure | 91 | Hours |
| Total Exposure | 3.791667 | Days |

TABLE 3B

Weekly Application

| Wash Time | 10 | Min |
|---|---|---|
| Washes/Week | 1 | washes |
| Weeks/Year | 52 | Weeks |
| Exposure Time/Year | 520 | min/year |
|  | 1.5 | Years |
| Total Exposure | 780 | minutes |
| Total Exposure | 13 | Hours |
| Total Exposure | 0.541667 | Days |

Figure 3:
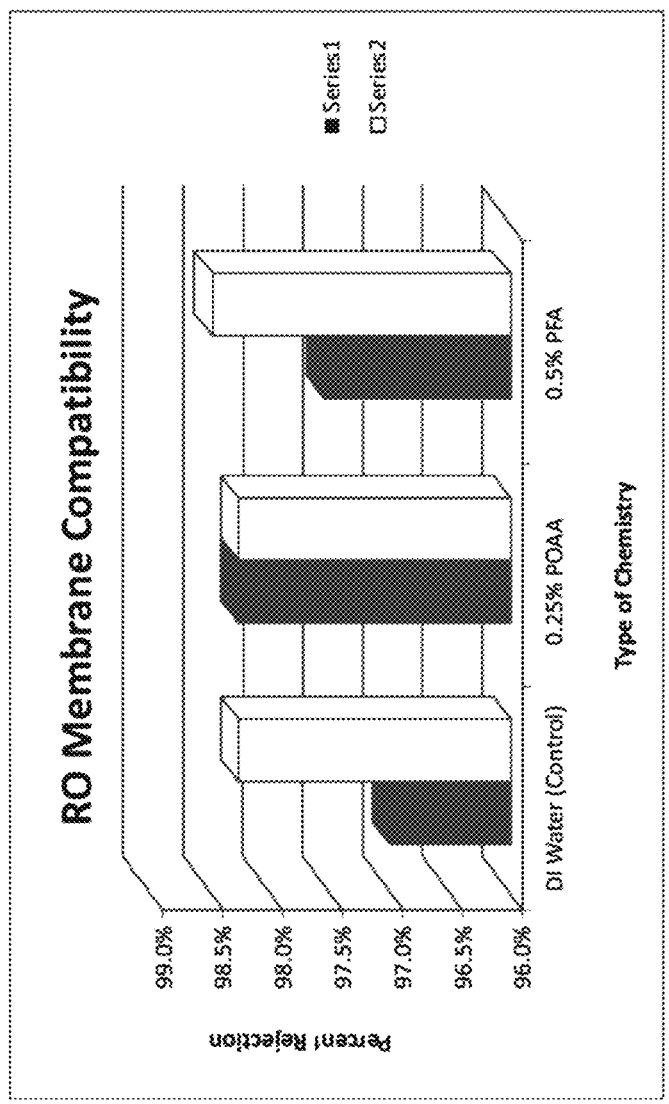
FIG. 3 shows membrane compatibility assessment of reverse osmosis membranes using a peroxyformic acid formulation according to an embodiment of the invention compared to commercially available peracid composition.

After the 4 days exposure the membranes are rinsed with DI water and placed on the Flat Sheet Membrane skid (Model M20). The membranes are rinsed with DI water for 24 hours at standard UF pressure and temperature. Once 24 hours is completed the membranes are subjected to alkaline conditioning step until solution pH is 11. 15.14 grams of NaCl is added to the recirculating water (2000 ppm NaCl) and the system is allowed to continue circulating. The conductivity of each permeate tube and feed is then measured and recorded and shown as percent rejection. The percent rejection is determined by (conductivity of the feed—conductivity of the permeate)/(conductivity of the feed). FIG. 3 shows two different runs (Series 1 and Series 2) testing the membrane compatibility of 30-1 (0.5%) being compared with POAA (0.25% product) and DI water control.

On average a brand new (virgin) RO membrane will measure at least (>) 97% rejection. This high percentage rejection refers to the percentage of permeate that is rejected, i.e. does not pass through the membrane. The higher the percentage, including above 97% rejection is a good indicator that an experimental formula displays membrane compatibility and does not damage the membrane. As can be seen in FIG. 3, all of the formulas evaluated have no impacts on the membranes comparing to water control through a virgin RO membrane. Formula 30-1 (0.5%) displayed an average percent rejection comparable to POAA.

In combination, Examples 1-4 show the exemplary formulas of the present invention may be particularly useful as an anti-microbial wash to dissolve mineral scale and kill biofilms while not decreasing the life of the membrane filtration elements. Indeed, the results shown in the above examples demonstrates that the exemplary compositions are superior against microorganisms and are very efficient in dissolving mineral scale on the membranes, furthermore, the compositions, under the evaluated conditions have no impacts on the membranes comparing to water control.

Example 4

The effects of PFA on reverse osmosis members which contain a poly-amide structure in comparison with known control chemicals were tested. Three different membranes were tested including Koch HRX, Hydranautics CPAS and Hydranautics ESPA2+. Membranes were soaked in duplicate, in chemistries according to Table 4.

TABLE 4

| Chemistry | Use Concentration |
|---|---|
| None | N/A |
| Chlorine and NaOH | 50 ppm Chlorine at pH = 11 |
| POAA | 1100 ppm |
| PFA | 300 ppm |

Membranes were then conditioned in Ultrasil 110 at a pH of 11 for 90 minutes at 50° C., followed by a rinse in DI water. Membranes were then prepared for testing according to Example 4 at the test conditions shown in Table 5.

TABLE 5

| Chemistry | Simulated Time | Soak Time (hr) | Temperature (F.) |
|---|---|---|---|
| None | N/A | 0 | 77 |
| Chlorine and NaOH | 3 Years | 936 | 122 |
| POAA | 3 Years | 234 | 77 |
| PFA | 1 Year | 78 | 77 |
| PFA | 3 Years | 234 | 77 |

Each of the chemistries, with the exception of PFA was refreshed daily. PFA was refreshed hourly. After the simulated exposure the membranes are rinsed with DI water and placed on the Flat Sheet Membrane skid (Model M20). The membranes were rinsed with DI water for 24 hours at standard UF pressure and temperature. Once 24 hours was completed the membranes were subjected to alkaline conditioning step until solution pH is 11. 15.14 grams of NaCl was added to the recirculating water (2000 ppm NaCl) and the system was allowed to continue circulating. The conductivity of each permeate tube and feed was then measured and recorded and shown as percent rejection. The percent rejection was determined by (conductivity of the feed—conductivity of the permeate)/(conductivity of the feed).

Figure 4:
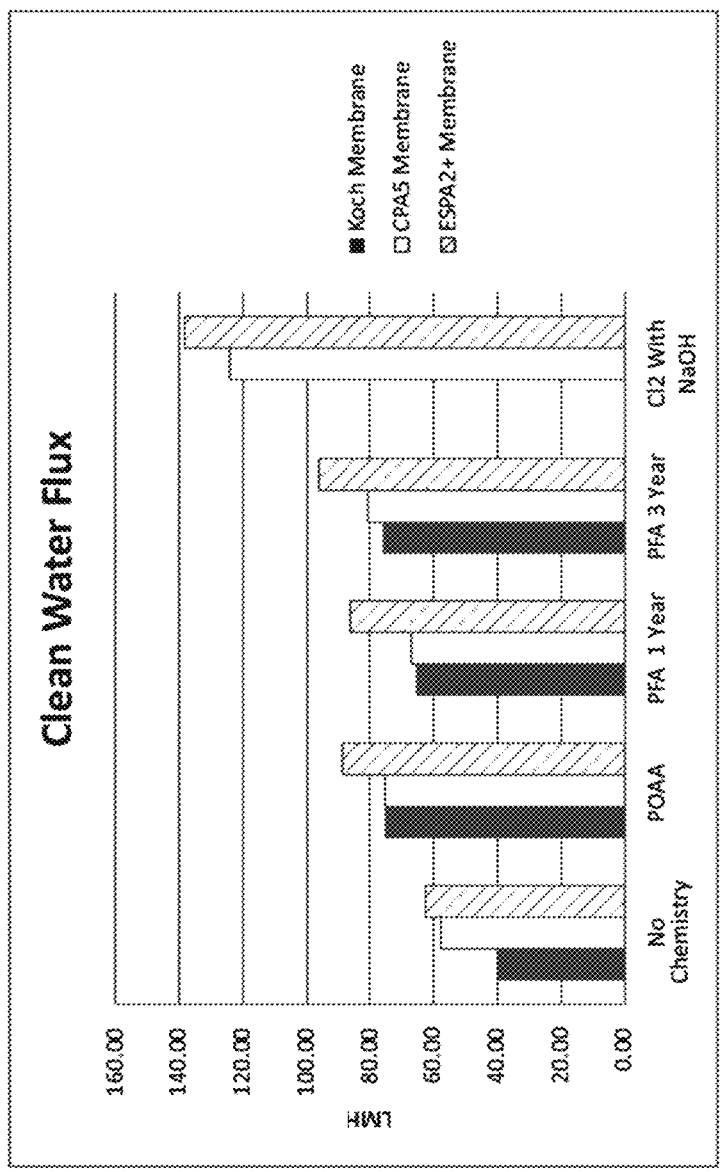
FIG. 4 shows membrane compatibility assessment via clean water flux measurements of reverse osmosis membranes using a peroxyformic acid formulation according to an embodiment of the invention compared to commercially available chemical control compositions.
Figure 5:
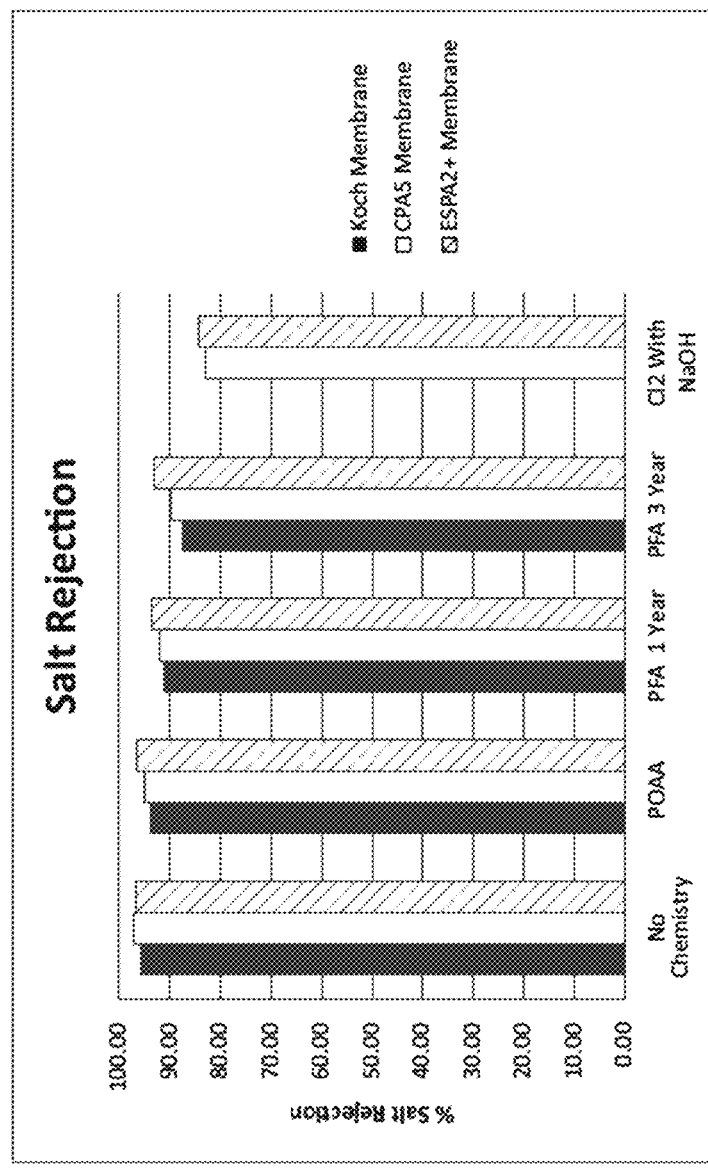
FIG. 5 shows membrane compatibility assessment via salt rejection measurements of reverse osmosis membranes using a peroxyformic acid formulation according to an embodiment of the invention compared to commercially available chemical control compositions.

FIG. 4 demonstrates the results of clean water flux for the tested membranes, while FIG. 5 depicts the salt rejection for each of the tested membranes. In combination, FIGS. 4-5 show the compatibility of the membranes with PFA. Table 6 proves the initial values for the flux and the salt rejections. Tables 7-8 represent the numerical results shown in FIGS. 4-5.

TABLE 6

| Membrane | Initial Water Flux (LMH) | Initial Salt Rejection (%) |
|---|---|---|
| Koch HRX | 40.08 | 95.73 |
| Hydranautics CPA5 | 57.72 | 97.02 |
| Hydranautics ESPA2+ | 62.53 | 96.58 |

TABLE 7

| Membrane | Water Flux (LMH) POAA | Salt Rejection (%) POAA | Water Flux (LMH) Chlorine | Salt Rejection (%) Chlorine |
|---|---|---|---|---|
| Koch HRX | 75.22 | 93.88 | * | * |
| Hydranautics CPA5 | 75.22 | 94.88 | 124.16 | 82.92 |
| Hydranautics ESPA2+ | 89.03 | 96.40 | 138.31 | 84.02 |

TABLE 8

| Membrane | Water Flux (LMH) PFA 1 YR | Salt Rejection (%) PFA 1 YR | Water Flux (LMH) PFA 3 YR | Salt Rejection (%) PFA 3 YR |
|---|---|---|---|---|
| Koch HRX | 65.40 | 91.26 | 75.84 | 87.50 |
| Hydranautics CPA5 | 66.99 | 91.89 | 80.58 | 89.71 |
| Hydranautics ESPA2+ | 86.13 | 93.50 | 96.38 | 93.01 |

As shown, PFA at 300 ppm is more compatible with a RO membrane than conventional chlorine treatment at 50 ppm and pH of 11. Membranes exposed for a simulated 1 year to PFA at 300 ppm provided comparable results to that of the commercially-available control peroxyacetic acid compositions at 3 years. Surprisingly, neither peroxyformic acid nor formic acid under the levels used was reactive to the membranes treated according to the embodiments of the invention. The demonstration of RO membrane compatibility signifies the chemistry and methods of the invention are suitable for the most sensitive of the membrane types (RO), indicating the compatibility for less sensitive (larger pore size range and filtration level) membranes, including microfiltration, ultrafiltration and nanofiltration. This is significant as the pore size of the membranes is the known factor of the membranes dictating compatibility (despite other differences in the membranes, including for examples construction material, e.g. adhesives).

Example 5

Additional testing was performed to compare percent biofilm reduction comparing glutaraldehyde and peroxyformic acid.

TABLE 9

| | Biofilm percent reductions | | |
|---|---|---|---|
| | Total biofilm | Viable biofilm | ATP |
| Glutaraldehyde-250 ppm | 58% | 81% | 94% |
| PFA-75 ppm active | 85% | 96% | 99% |

Figure 6:
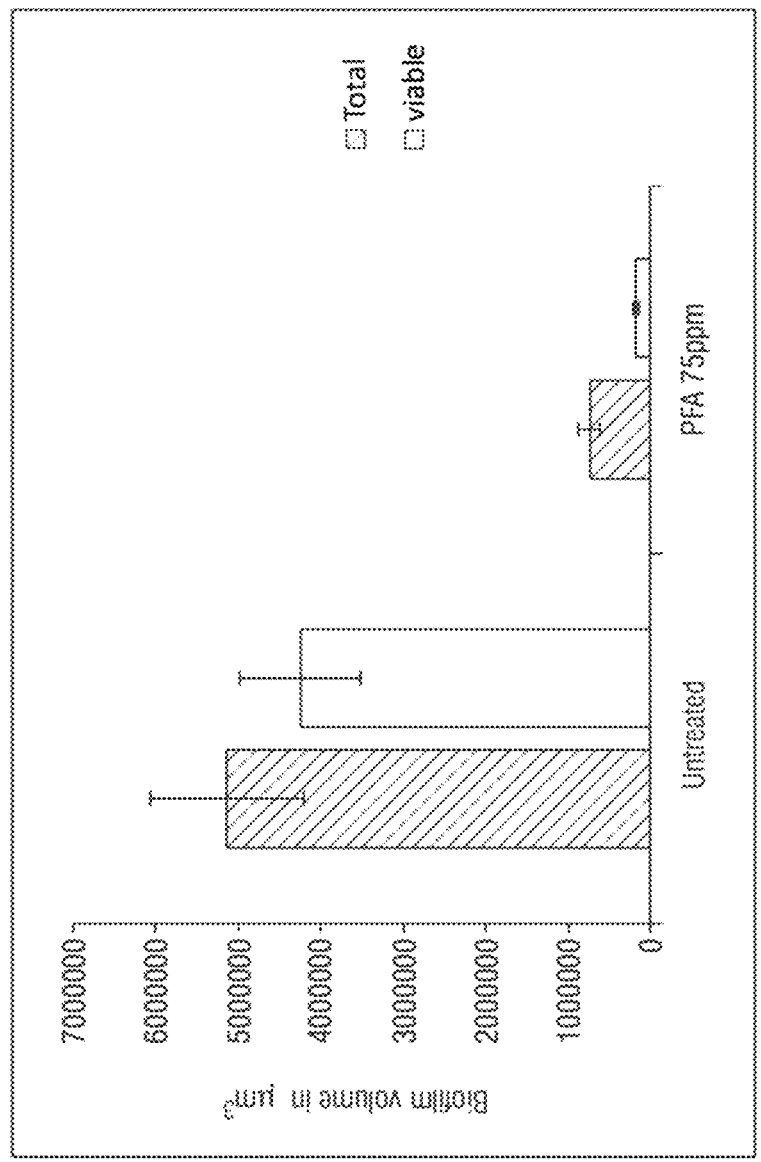
FIG. 6 shows the results of statistical analysis on volume of biofilm performed on oil and gas biofilm grown before and after treatment with peroxyformic acid

As shown in Table 9 and FIG. 6, the biofilm volume in terms of total biofilm and viable biofilm is more effectively reduced according to the present invention when compared to traditional glutaraldehyde cleaning components.

Example 6

The effectiveness of the present invention against a *Pseudomonas* biofilm in a continuous in-line simulation was also tested according to the conditions shown in Table 10. Concentration X time parameter was kept the same for all concentrations tested: 25 ppm was treated for 60 minutes, 50 ppm for 30 minutes, 100 ppm for 15 minutes, 100 ppm for 7.5 minutes and 200 ppm for 3.7 minutes, respectively. The concentrations here refer to the product concentration employed; for example the 100 ppm peroxyformic acid composition is equivalent to 15 ppm PFA active.

TABLE 10

| Concentration as product final composition | Time (min) | Concentration x Flow | Flow Rate (mL/min) |
|---|---|---|---|
| 400 | 3.75 | 1500 | 5 |
| 200 | 7.5 | 1500 | 5 |
| 100 | 15 | 1500 | 5 |
| 50 | 30 | 1500 | 5 |
| 25 | 60 | 1500 | 5 |

Microbial concentration following treatment was collected and all conditions according the present invention provided superior microbial reduction in comparison with UT, a conventional cleaning protocol.

Example 7

As previously discussed, free chlorine concentration is a concern for membrane use and cleaning as excessive exposure to free chlorine can make membranes prone to breakage due to oxidation. As such, it is an object of the present invention to ensure that in presence of source waters where are salinized or naturally salinized, i.e., sea water, the free chlorine concentration does not increase to undesirable levels.

Figure 7:
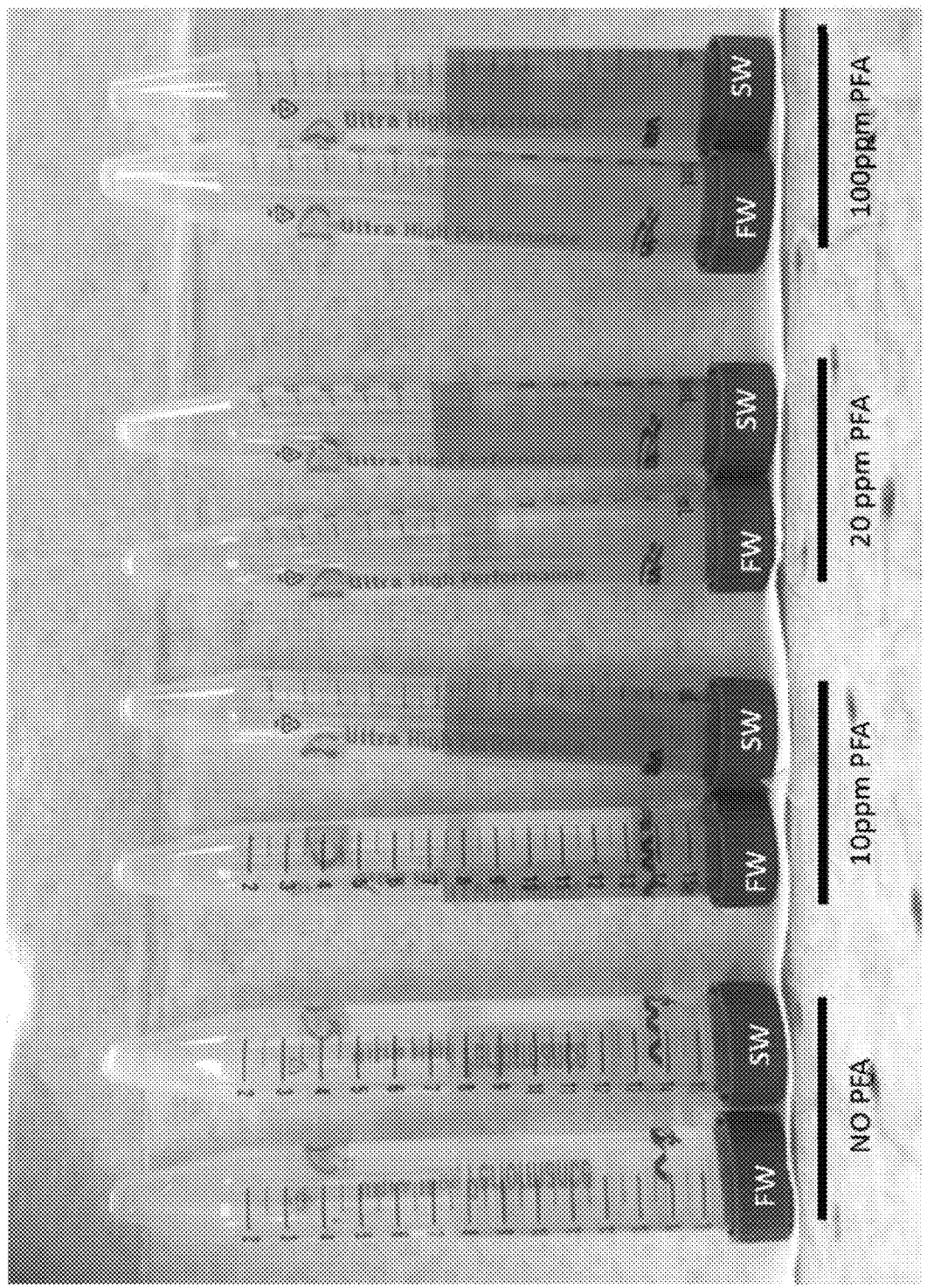
FIG. 7 shows the results of the DPD assay described in Example 7. Notably, the example utilizing salt water (SW) does not substantially increase the presence of free chlorine as compared to fresh water (FW)
Figure 8:
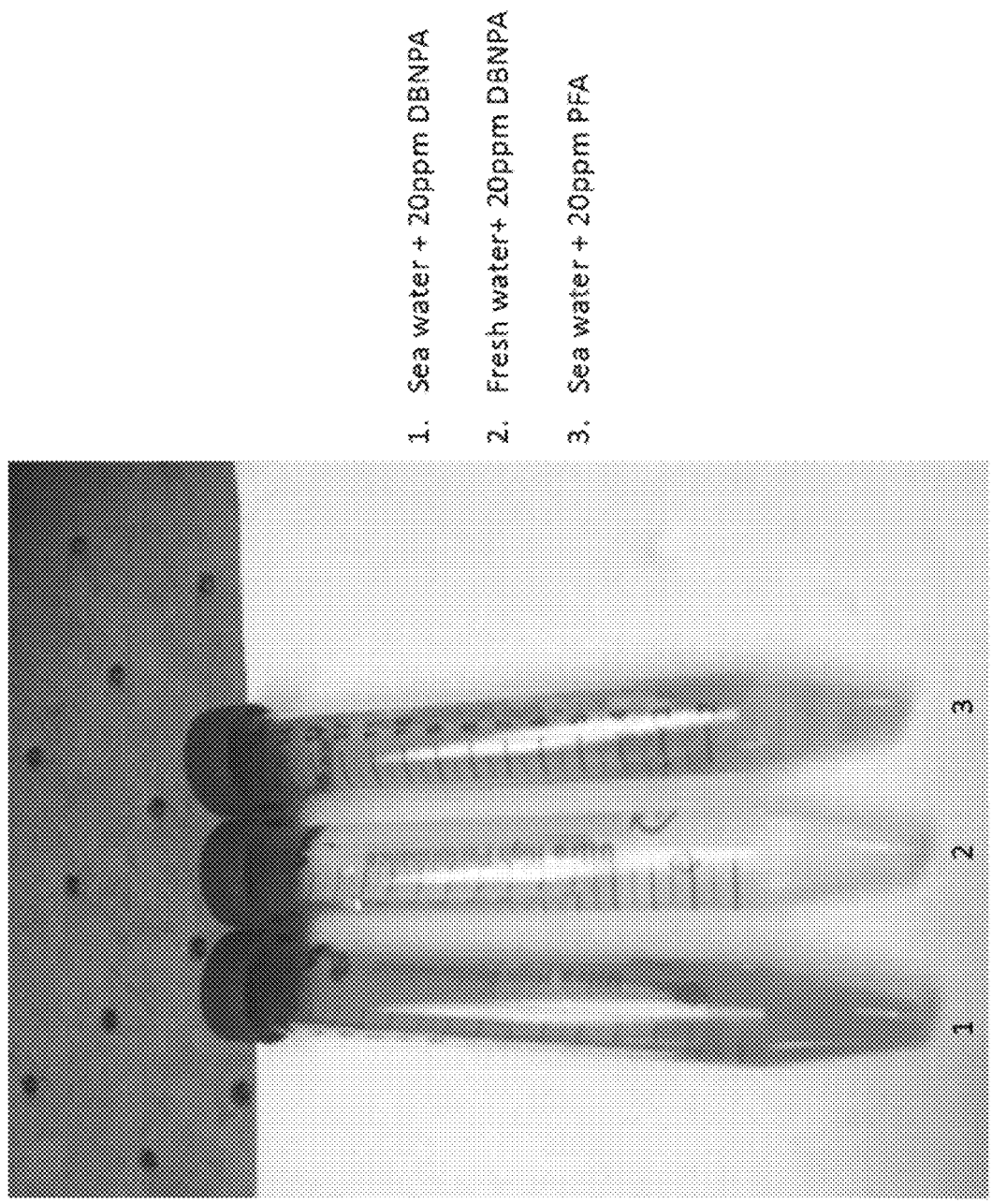
FIG. 8 shows the results of the DPD assay described in Example 7. Notably, the present invention results in a substantially lower free chlorine composition in comparison with DBNPA.

A DPD based assay was used to quantitate free chlorine in test samples according to the present invention as well as 2,2-dibromo-3-nitrilopropionamide (DBNPA), which is commonly used as a quick-kill biocide that easily hydrolyzes under both acidic and alkaline conditions. Replacement or reduction of the DBNPA is beneficial due to environmental concerns associated with the biocide. Free chlorine oxidizes DPD, changing the color from colorless to pink via use of a Wüster dye. Further, the reaction is pH dependent. DPD and the appropriate buffer are packaged together in DPD Free Chlorine Reagent Power (Cat. No. 21978-46). Contents of the package were dissolved with 5 mLs of deionized, high purity MilliQ water before use. Results are shown in FIGS. 7-8. As shown in FIG. 7, the presence of salt water creates a minor color change indicating the additional presence of salination does not substantially impact the free chlorine generation when compositions according the present invention are employed. FIG. 8 depicts that when comparing the present invention to that of DBNPA, the present invention provides substantially less free chlorine generation. The figures are shown in grey scale, with the darker color indicating a darker pink color change according to the example.

While this invention may be embodied in many different forms, there are described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments mentioned herein, described herein and/or incorporated herein. In addition the invention encompasses any possible combination that also specifically excludes any one or some of the various embodiments mentioned herein, described herein and/or incorporated herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

What is claimed is:

1. A method for treating a membrane system comprising: contacting a membrane with a peroxyformic acid composition comprising peroxyformic acid, formic acid, hydrogen peroxide, an acidulant and an anionic surfactant, wherein the composition is membrane compatible and does not damage the membrane as measured by a decrease in flux of the membrane; and removing biofilm, microbial growth and/or mineral deposits from the membrane surface, wherein the contacting is intermittent and occurs daily, bi-weekly, or weekly.

2. The method of claim 1, wherein the membrane is a reverse osmosis membrane, nanofiltration membrane, ultrafiltration membrane, or a microfiltration membrane.

3. The method of claim 1, wherein the membrane comprises cellulose, cellulose acetate, nitrocellulose, polysulfone, polyethersulfone, fully aromatic polyamide, polyvinylidene fluoride, polytetrafluoroethylene, polyacrylnitrile, polypropylene, carbon, alpha-aluminum oxide, zirconium oxide, ceramic and/or stainless steel.

4. The method of claim 1, wherein the peroxyformic acid composition comprises between about 0.001% (w/w) and about 5% (w/w) hydrogen peroxide, and between about 0.0001% (w/w) to about 20% (w/w) peroxyformic acid.

5. The method of claim 1, further comprising at least one additional step of a first product removal step before the membrane is contacted with the peroxyformic acid composition, a pre-rinse step of washing the membrane with water, a soak step of washing the membrane, and/or an additional treatment cycle(s) comprising an acidic treatment, an enzymatic treatment, an alkaline treatment and/or a neutral treatment either before or after the peroxyformic acid composition contacts the membrane.

6. The method of claim 1, wherein the peroxyformic acid composition is free of 2,2-dibromo-3-nitrilopropionamide.

7. The method of claim 1, wherein the acidulant is nitric acid, sulfuric acid, phosphoric acid, and/or methyl sulfonic acid.

8. The method of claim 1, wherein the is anionic surfactant is an alkyl aryl sulfonate, alkyl sulfonate, alkyl ether sulfate, alkyl sulfate, and/or alcohol sulfate.

9. The method of claim 8, wherein the alkyl aryl sulfonate is a linear alkyl benzene sulfonate and/or xylene sulfonate.

10. The method of claim 1, wherein the membrane is fouled with a hydrocarbon, microorganism, biofilm, mineral scale, and/or iron sulfide.

11. The method of claim 1, wherein the peroxyformic acid composition is generated in situ by contacting formic acid with hydrogen peroxide, wherein before said contacting, the ratio between the concentration of said formic acid (w/v) and the concentration of said hydrogen peroxide (w/v) is about 2 or higher, and the ratio between the concentration of said peracid (w/w) and the concentration of hydrogen peroxide (w/w) in said formed resulting aqueous composition reaches about 2 or higher within about 1 hour of said contacting.

12. The method of claim 11, wherein the formic acid is provided in a first aqueous composition and is contacted with a second aqueous solution of the hydrogen peroxide.

13. The method of claim 11, wherein the method prevents the build-up of microorganisms and/or membrane deposits on the membrane.

14. The method of claim 1, wherein the peroxyformic acid composition further comprises a wetting agent, a chelant, solvent and/or an additional surfactant.

15. The method of claim 1, wherein the contacting step lasts between 15 minutes and 15 hours.

16. The method of claim 1, wherein the peroxyformic acid composition does not generate chlorine species.

17. The method of claim 1, wherein the membrane is contacted with between about 1 ppm to about 300 ppm actives of peroxyformic acid.

18. The method of claim 1, wherein the peroxyformic acid composition comprises an additional peroxycarboxylic acid.

* * * * *

UNITED STATES PATENT AND TRADEMARK OFFICE
CERTIFICATE OF CORRECTION

PATENT NO. : 11,647,747 B2
APPLICATION NO. : 17/302678
DATED : May 16, 2023
INVENTOR(S) : Junzhong Li et al.

Page 1 of 1

It is certified that error appears in the above-identified patent and that said Letters Patent is hereby corrected as shown below:

In the Claims

In Column 32, Claim 8, at Line 65:
DELETE: "is"

Signed and Sealed this
Twenty-sixth Day of December, 2023

*Katherine Kelly Vidal*

Katherine Kelly Vidal
*Director of the United States Patent and Trademark Office*